United States Patent
Hynd et al.

(10) Patent No.: US 10,822,342 B2
(45) Date of Patent: Nov. 3, 2020

(54) PYRAZOLOPYRIMIDINE DERIVATIVES AS NIK INHIBITORS

(71) Applicant: Janssen Pharmaceutica NV, Beerse (BE)

(72) Inventors: George Hynd, Essex (GB); Patrizia Tisselli, Essex (GB); Calum MacLeod, Essex (GB); Samuel Edward Mann, Essex (GB); Terry Aaron Panchal, Essex (GB); John Gary Montana, Essex (GB); Stephen Colin Price, Essex (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/265,679

(22) Filed: Feb. 1, 2019

(65) Prior Publication Data

US 2019/0169198 A1    Jun. 6, 2019

Related U.S. Application Data

(62) Division of application No. 15/520,346, filed as application No. PCT/EP2015/074431 on Oct. 22, 2015, now Pat. No. 10,221,180.

(30) Foreign Application Priority Data

Oct. 23, 2014  (EP) ................................. 14190073

(51) Int. Cl.
  *C07D 487/04* (2006.01)
  *C07D 519/00* (2006.01)

(52) U.S. Cl.
  CPC ......... *C07D 487/04* (2013.01); *C07D 519/00* (2013.01)

(58) Field of Classification Search
  None
  See application file for complete search history.

(56) References Cited

U.S. PATENT DOCUMENTS

| | | | |
|---|---|---|---|
| 5,169,947 | A | 12/1992 | Macor |
| 7,468,375 | B2 | 12/2008 | Dress et al. |
| 9,643,964 | B2 | 5/2017 | Hynd et al. |
| 2011/0086834 | A1 | 4/2011 | Chen et al. |
| 2012/0214762 | A1 | 8/2012 | Staben et al. |
| 2016/0075699 | A1 | 3/2016 | Hynd et al. |
| 2016/0229851 | A1 | 8/2016 | Hynd et al. |
| 2016/0257679 | A1 | 9/2016 | Hynd et al. |

FOREIGN PATENT DOCUMENTS

| | | |
|---|---|---|
| JP | 2011-525915 A | 9/2011 |
| JP | 2011-526931 A | 10/2011 |
| WO | WO 2007/058850 A2 | 5/2007 |
| WO | WO 2007/058850 A3 | 5/2007 |
| WO | WO 2009/092431 A1 | 7/2009 |
| WO | WO2009/158011 * | 12/2009 |
| WO | WO 2009/158011 A1 | 12/2009 |
| WO | WO 2010/003133 A2 | 1/2010 |
| WO | WO 2010/003133 A3 | 1/2010 |
| WO | WO 2010/042337 A1 | 4/2010 |
| WO | WO 2010/051781 A1 | 5/2010 |
| WO | WO 2011/050245 A1 | 4/2011 |
| WO | 2012/123522 A1 | 9/2012 |
| WO | WO 2014/174021 A1 | 10/2014 |
| WO | WO 2015/044267 A1 | 4/2015 |
| WO | WO 2015/044269 A1 | 4/2015 |
| WO | WO 2016/062789 A1 | 4/2016 |
| WO | WO 2016/062790 A1 | 4/2016 |
| WO | WO 2016/062791 A1 | 4/2016 |
| WO | WO 2016/062792 A1 | 4/2016 |

OTHER PUBLICATIONS

. Luo et al., 36 Cell, 823-837 (2009) (Year: 2009).*
T. Soussi 60 Cancer Research, 1777-1788 (2000) (Year: 2000).*
P. Lissoni et al., 7 Cancer Research, 397-401 (2009) (Year: 2009).*
National Cancer Institute (http://www.cancer.gov/) (Downloaded May 29, 2014) (Year: 2014).*
F. Bunz, Principles of Cancer Genetics 1-47, 1 (2008) (Year: 2008).*
P.K. Kuppen et al., 115 Histochemistry and Cell Biology, 67-72 (2001) (Year: 2001).*
R.J. Kok, 25 Pharmaceutical Research, 2413-2415 (2008) (Year: 2008).*
Z. Ghiassi-Nejad et al. 2 Expert Review of Gastroenterology & Hepatology, 803-816 (2008) (Year: 2008).*
C.J. O'Brien, Head and Neck, 946-952 (2003) (Year: 2003).*
H. Nandeesha et al., 370 Clinica Chimica Acta, 89-93 (2006) (Year: 2006).*
S. Yamada et al., 242 The Journal of Pharmacology and Experimental Therapeutics, 326-330 (1987) (Year: 1987).*
J. Kim et al., 150 Endocrinology, 3576-3583 (2009) (Year: 2009).*
J.D. Cashman et al., 171 Journal of Surgical Research, 495-503 (2011) (Year: 2011).*
T. Yamamoto et al., 90 Proceedings of the National Academy of Sciences, 1814-1818 (1993) (Year: 1993).*
Y-M Sun et al., 433 Biochemical and Biophysical Research Communications, 359-361 (2013) (Year: 2013).*
A. Kim et al., 2014 International Journal of Nephrology and Renovascular Disease, 361-381 (2014) (Year: 2014).*

(Continued)

*Primary Examiner* — Dennis Heyer

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

12 Claims, No Drawings

(56) References Cited

OTHER PUBLICATIONS

Kinase Inhibitors, Methods in Molecular Biology 795 (B. Kuster ed., 2012) (Year: 2012).*
H. Jing et al., 37 Molecular Cells, 189-195 (2014) (Year: 2014).*
N. D. Perkins, 12 Nature Reviews Cancer, 121-132 (2012) (Year: 2012).*
C. Carbone et al., 16 Expert Opinion on Therapeutic Targets, S1-S10 (2012) (Year: 2012).*
Y. Herishanu et al., 117 Blood, 563-574 (2011) (Year: 2011).*
F. Pacifico et al., 321 Molecular and Cellular Endocrinology, 29-35 (2010) (Year: 2010).*
T. Tremlay et al., 62 Metabolism Clinical and Experimental, S2-S5 (2013) (Year: 2013).*
U. McDermott et al., 27 Journal of Clinical Oncology, 5650-5659 (2009) (Year: 2009).*
C.L. Sawyers, Nature, 548-552 (2008) (Year: 2008).*
C.M. Coughlin et al., Breast Cancer Research Treatment, 1-11 (2010) (Year: 2010).*
Thu, Y.M., et al., "NF-κB inducing kinase: A key regulator in the immune system and in cancer", Cytokine & Growth, (2010), vol. 21, pp. 213-226.
Annunziata, C.M., et al., "Frequent Engagement of the Classical and Alternative NF-κB Pathways by Diverse Genetic Abnormalities in Mulitiple Myeloma", Cancer Cell, (2007), vol. 12, pp. 115-130.
Keats, J.J., et al., "Promiscuous Mutations Activate the Noncanonical NF-κB Pathway in Multiple Myeloma", Cancer Cell, (2007), vol. 12, pp. 131-144.
Demchenko, Y.N., et al., "Classical and/or alternative NF-κB pathway activation in multiple myeloma", Blood, (2010), vol. 115, No. 17, pp. 3541-3552.
Ranuncolo, S.M., et al., "Hodgkin lymphoma requires stabilized NIK and constitutive RelB expression for survival", Blood, (2012), vol. 120, No. 18, pp. 3756-3763.
Saitoh, Y., et al., "Overexpressed NF-κB-inducing kinase contributes to the tumorigenesis of adult T-cell leukemia and Hodgkin Reed-Sternberg cells", Blood, (2008), vol. 111, No. 10, pp. 5118-5129.
Rosebeck, S., et al., "Cleavage of Nik by the API2-MALT1 Fusion Oncoprotein Leads to Noncanonical NF-κB Activiation", Science, (2011), vol. 331, pp. 4468-4472.
Pham, L.V., et al., "Constitutive BR3 receptor signaling in diffuse, large B-cell lymphomas stabilizes nuclear factor-κb-inducing kinase while activating both canonical and alternative nuclear factor-κB pathways", Blood, (2011), vol. 117, No. 1, pp. 200-210.
Nishina, T., et al., "NIK is involved in constitutive activation of the alternative NF-κB pathway and proliferation of pancreatic cancer cells", Biochem. Bioph. Res., (2009), vol. 388, pp. 96-101.
Yamamoto, M., et al., "Epigenetic alteration of the NF-κB-inducing kinase (NIK) gene is involved in enhanced NIK expression in basal-like breast cancer", Cancer Science, (2010), vol. 101, No. 11, pp. 2391-2397.
Thu, Y.M., et al., "NF-κB inducing kinase (NIK) modulates melanoma tumorigenesis by regulating expression of pro-survival factors through the β-catenin pathway", Oncogene, (2012), vol. 31, pp. 2580-2592.
Allen, I.C., et al., "NLRP12 Suppresses Colon Inflammation and Tumorigenesis through the Negative Regulation of Noncanonical NF-κB Signaling", Immunity, (2012), vol. 36, pp. 742-754.
Bhattacharyya, S., et al., "Tumor Necrosis Factor a-induced Inflammation Is Increased but Apoptosis Is Inhibited by Common Food Additive Carrageenan", Journal of Biological Chemistry, (2010), vol. 285, No. 50, pp. 39511-39522.
Shuto, T., et al., "Activation of NF-κB by nontypeable Hemophilus influenza is medicated by toll-like receptor 2-TAK1-dependent NIK-IKKα/β-IκBα and MKK3/6-p38 MAP kinase signaling pathways in epithelial cells", PNAS, (2001), vol. 98, No. 15, pp. 8774-8779.
Wixted, W.E., et al., "A model to identify novel targets involved in oxidative stress-induced apoptosis in human lung epithelial cells by RNA interference", Toxicology in Vitro, (2010), vol. 24, pp. 310-318.
Bitar, M.S., et al., "Inflammation and apoptosis in aortic tissues of aged type II diabetes: Amelioration with αlipoic acid through phosphatidylinositol 3-kinase/Akt-dependent mechanism", Life Science, (2010), vol. 86, pp. 844-853.
Zhao, Y., et al., "FN-κB-Inducing Kinase Increases Renal Tubule Epithelial Inflammation Associated with Diabetes", Experimental Diabetes Research, (2011), vol. 2011, pp. 1-9.
Choudhary, S., et al., "NF-κB-Inducing Kinase (NIK) Mediates Skeletal Muscle Insulin Resistance: Blockade by Adiponectin", Endocrinology, (2011), vol. 152, No. 10, pp. 3622-3627.
Aya, K., et al., "NF-κB-inducing kinase controls lymphocyte and osteoclast activities in flammatory arthritis", The Journal of Clinical Investigation, (2005), vol. 115, No. 7, pp. 1848-1854.
Yang, C., et al., "NIK Stabilization in Osteoclasts Results in Osteoporosis and Enhanced Inflammatory Osteolysis", PLoS ONE, (2010), vol. 5, No. 11, p. e15383.
T.W. Greene, et al., "Greene's Protective Groups in Organic Synthesis" Fourth Edition, (2007), Table of Contents, John Wiley & Sons, Inc.
Greene, T.W., "Protective Groups in Organic Synthesis", (1991) John Wiley & Sons, New York.
Fustero, S., et al., "From 2000 to Mid-2010: A Fruitful Decade for the Synthesis of Pyrazoles", Chemical Reviews, (2011), vol. 111, pp. 6984-7034.
Gennaro, A.R., Remington's 18th ed., Mack Publishing Company, (1990) see especially Part 8: Pharmaceutical preparations and their Manufacture, pp. 1435-1712.
Chung, S., et al., "NF-κB Inducing Kinase, NIK Mediates Cigarette Smoke/TNFα-Induced Histone Acetylation and Inflammation Through Differential Activation of IKKS", PLoS ONE, (2011), vol. 6, No. 8, pp. e23488.
Baraldi, P.G., et al., "Pyrrolo-And Pyrazolo-[3,4-e][1,2,4]Triazolo[1,5-c]Pyrimidines As Adenosine Receptor Antagonists", Bioorganic & Medicinal Chemistry, (2012), vol. 20, pp. 1046-1059.
Merour, J.Y, et al., "Recent Advances in the Synthesis and Properties of 4-, 5-, 6- or 7-Azaindoles", Tetrahedron, (2013), vol. 69, pp. 4767-4834.
Taber, D.F., et al., "Indole Synthesis: A Review and Proposed Classification", Tetrahedron, (2011), vol. 67, pp. 7195-7210.
Elguero, J., "Comprehensive Heterocyclic Chemistry II", Chem. Rev., (1996), vol. 2011, No. 111, pp. 6984-7034, Pergamon Press: Oxford.
Greene, T.W., et al., "Greene'S Protective Groups in Organic Synthesis", 4th ed., (2007), Wiley-Interscience, Hoboken, New Jersey.
J. Luo et al., 36 Cell, pp. 823-837 (2009).
T. Soussi 60 Cancer Research, pp. 1777-1788 (2000).
P. Lissoni et al. 7 Cancer Research, pp. 397-401 (2009).
National Cancer Institute (http://www.cancer.gov/) (Downloaded May 29, 2014).
F. Bunz, Principles of Cancer Genetics pp. 1-47, 1 (2008).
P.K. Kuppen et al., 115 Histochemistry and Cell Biology, pp. 67-72 (2001).
R.J. Kok, 25 Pharmaceutical Research, pp. 2413-2415 (2008).
Z. Ghiassi-Nejad et al. 2 Expert Review of Gastroenterology & Hepatology, pp. 803-816 (2008).
C.J. O'Brien, Head and Neck, pp. 946-952 (2003).
H. Nandeesha et al., 370 Clinica Chimica Acta, pp. 89-93 (2006).
S. Yamada et al., 242 The Journal of Pharmacology and Experimental Therapeutics, pp. 326-330 (1987).
J. Kim et al., 150 Endocrinology, pp. 3576-3583 (2009).
J.D. Cashman et al., 171 Journal of Surgical Research, pp. 495-503 (2011).
Yamamoto et al., 90 Proceedings of the National Academy of Sciences, pp. 1814-1818 (1993).
A. Lim et al., 2014 International Journal of Nephrology and Renovascular Disease, pp. 361-381 (2014).
Kinase Inhibitors, Methods in Molecular Biology 795 (B. Kuster ed., 2012).

(56) References Cited

OTHER PUBLICATIONS

H. Jing et al., 37 Molecular Cells, pp. 189-195 (2014).
N.D. Perkins, 12 Nature Reviews Cancer, pp. 121-132 (2012).
C. Carbone et al., 16 Expert Opinion on Therapeutic Targets, pp. S1-S10 (2012).
Y. Herishanu et al., 117 Blood, pp. 563-574 (2011) (chronic lymphocytic leukemia).
F. Pacifico et al. 321 Molecular and Cellular Endocrinology, pp. 29-35 (2010).
J. Tremblay et al., 62 Metabolism Clinical and Experimental, pp. S2-S5 (2013).
U. McDermott et al., 27 Journal of Clinical Oncology, pp. 5650-5659 (2009).
C.L. Sawyers, Nature, pp. 548-552 (2008).
C.M. Coughlin et al., Breast Cancer Research Treatment, pp. 1-11 (2010).
International Search Report PCT/EP2014/070484 dated Oct. 23, 2014.
International Search Report PCT/EP2014/070489 dated Nov. 6, 2014.
International Search Report PCT/EP2015/074430 dated Dec. 18, 2015.
International Search Report PCT/EP2015/074431 dated Nov. 25, 2015.
International Search Report PCT/EP2015/074433 dated Nov. 25, 2015.
International Search Report PCT/EP2015/074437 dated Dec. 21, 2015.

* cited by examiner

PYRAZOLOPYRIMIDINE DERIVATIVES AS NIK INHIBITORS

CROSS REFERENCE TO RELATED APPLICATIONS

This application is a divisional of U.S. application Ser. No. 15/520,346, filed Apr. 19, 2017, which is a national stage of PCT Application No. PCT/EP2015/074431, filed Oct. 22, 2015, which claims priority for EPO Patent Application No. 14190073.8, filed Oct. 23, 2014, all of which are hereby incorporated by reference in their entirety.

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders including obesity and diabetes, and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK has a role in both but has been shown to be indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226)

Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *ibid* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129). It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010. 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2011, 1-13). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable Hemophilus influenza (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et al. Toxicol. *In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand—stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS One* 2010, 5, 1-9, e15383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune and alloresponses, like GVHD (Graft Versus Host Disease) and transplant rejection, without crippling the immune system as severely as do inhibitors of canonical NF-κB activation.

WO2010/042337 describes novel 6-azaindole aminopyrimidine derivatives having NIK inhibitory activity.

WO2009/158011 describes alkynyl alcohols as kinase inhibitors.

WO2012/123522 describes 6,5-heterocyclic propargylic alcohol compounds and uses therefor.

DESCRIPTION OF THE INVENTION

The present invention concerns novel compounds of Formula (I):

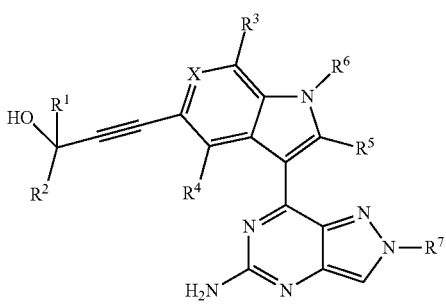

and tautomers and stereoisomeric forms thereof, wherein $R^1$ is selected from the group of hydrogen; $C_{1-4}$alkyl; and $C_{1-4}$alkyl substituted with one or more fluoro substituents;

$R^2$ is selected from the group of hydrogen; $C_{1-4}$alkyl; $C_{1-4}$alkyl substituted with one or more fluoro substituents; $C_{3-6}$cycloalkyl; and Het$^1$;

or $R^1$ and $R^2$ together with the carbon atom to which they are attached form a $C_{3-6}$cycloalkyl;

Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;

X is N or $CR^9$;

$R^9$ is selected from hydrogen and halogen;

$R^3$ is selected from the group of hydrogen; halogen; cyano; $C_{3-6}$cycloalkyl; $C_{1-6}$alkyl;

Het$^4$; $C_{1-6}$alkyl substituted with one or more fluoro substituents; —$OC_{1-6}$alkyl;

—$OC_{1-6}$alkyl substituted with one or more fluoro substituents; and $C_{1-6}$alkyl substituted with one substituent selected from —$NR^{3a}R^{3b}$ and —$OC_{1-4}$alkyl;

Het$^4$ is a heteroaryl selected from the group of piperidinyl, tetrahydropyranyl, pyrrolidinyl, tetrahydrofuranyl, azetidinyl, piperazinyl, morpholinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

$R^{3a}$ and $R^{3b}$ are each independently selected from hydrogen and $C_{1-4}$alkyl;

$R^4$ is hydrogen;

$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of —$NR^{5a}R^{5b}$, —$OC_{1-4}$alkyl, and Het$^5$;

$R^{5a}$ and $R^{5b}$ are each independently selected from the group of hydrogen and $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

$R^6$ is selected from the group of hydrogen; Het$^2$; $R^8$; $C_{1-6}$alkyl optionally substituted with one Het$^3$; and $C_{2-6}$alkyl substituted with one or more substituents independently selected from the group of fluoro, —$NR^{6a}R^{6b}$, and —$OR^{6c}$c, $R^{6a}$, $R^{6b}$ and $R^{6c}$ are each independently selected from hydrogen and $C_{1-6}$alkyl;

Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl,
$C_{1-4}$alkyl substituted with one $C_{3-6}$cycloalkyl,
and $C_{1-4}$alkyl substituted with one or more fluoro substituents;

$R^8$ is $C_{3-6}$cycloalkyl optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$R^7$ is selected from the group of hydrogen, $C_{1-6}$alkyl, $C_{3-6}$cycloalkyl and $C_{1-4}$alkyl substituted with one —$OC_{1-4}$alkyl;

and the pharmaceutically acceptable salts, and the solvates thereof.

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term '$C_{2-6}$alkyl' as used herein as a group or part of a group represents a straight or branched chain saturated hydrocarbon radical having from 2 to 6 carbon atoms such as ethyl, n-propyl, isopropyl, n-butyl, s-butyl, t-butyl, n-pentyl, n-hexyl, 2-methylbutyl and the like.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

The term '$C_{1-4}$alkyloxy' as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term '$C_{1-6}$alkyl substituted with one or more substituents' as used herein as a group or part of a group refers to a $C_{1-6}$alkyl group as defined herein wherein one or more than one hydrogen atom is replaced with another group. The term therefore includes monosubstituted $C_{1-6}$alkyl and also polysubstituted $C_{1-6}$alkyl. There may be one, two, three or more hydrogen atoms replaced with a substituent, so the fully or partially substituted $C_{1-6}$alkyl may have one, two, three or more substituents. Examples of such groups wherein the substituent is for example, fluoro include fluoromethyl, difluoromethyl, trifluoromethyl, fluoroethyl, trifluoroethyl and the like.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

C(O) or C(=O) represents a carbonyl moiety.

$S(O)_2$ or $SO_2$ represents a sulfonyl moiety.

Substituents covered by the term "$Het^x$" (where x is an integer; or $Het^x$ refers to $Het^{1a}$, $Het^{1b}$, $Het^{2a}$, ... ), "heterocyclyl" or "heteroaryl" may be attached to the remainder of the molecule of Formula (I) through any available ring carbon or heteroatom as appropriate, if not otherwise specified.

Whenever substituents are represented by chemical structure, "—" represents the bond of attachment to the remainder of the molecule of Formula (I).

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Conversely, said salt forms can be converted into the free base form by treatment with an appropriate base.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Conversely, said salt forms can be converted into the free acid forms by treatment with an appropriate acid.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^{2}H$ (D), $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

The present invention relates in particular to compounds of Formula (I) as defined herein, and tautotners and stereoisomeric forms thereof, wherein $R^1$ is selected from the group of hydrogen; $C_{1-4}$alkyl; and $C_{1-4}$alkyl substituted with one or more fluoro substituents;

$R^2$ is selected from the group of $C_{1-4}$alkyl; $C_{1-4}$alkyl substituted with one or more fluoro substituents; $C_{3-6}$cycloalkyl; and $Het^1$;

or $R^1$ and $R^2$ together with the carbon atom to which they are attached form a $C_{3-6}$cycloalkyl;

$Het^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;

X is N or $CR^9$;

$R^9$ is selected from hydrogen and halogen;

$R^3$ is selected from the group of hydrogen; halogen; cyano; $C_{3-6}$cycloalkyl; $C_{1-6}$alkyl;

$C_{1-6}$alkyl substituted with one or more fluoro substituents; $-OC_{1-6}$alkyl; $-OC_{1-6}$alkyl substituted with one or more fluoro substituents; and $C_{1-6}$alkyl substituted with one substituent selected from $-NR^{3a}R^{3b}$ and $-OC_{1-4}$alkyl;

$R^{3a}$ and $R^{3b}$ are each independently selected from hydrogen and $C_{1-4}$alkyl;

$R^4$ is hydrogen;

$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of $-NR^{5a}R^{5b}$, and $-OC_{1-4}$alkyl;

$R^{5a}$ and $R^{5b}$ are each independently selected from the group of hydrogen and $C_{1-4}$alkyl;

$R^6$ is selected from the group of hydrogen; $Het^2$; $R^8$; $C_{1-6}$alkyl optionally substituted with one $Het^3$; and $C_{2-6}$alkyl substituted with one or more substituents independently selected from the group of fluoro, $-NR^{6a}R^{6b}$, and $-OR^{6c}$, $R^{6a}$, $R^{6b}$ and $R^{6c}$ are each independently selected from hydrogen and $C_{1-6}$alkyl;

$Het^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

$R^8$ is $C_{3-6}$cycloalkyl optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$R^7$ is selected from the group of hydrogen, $C_{1-6}$alkyl, $C_{3-6}$cycloalkyl and $C_{1-4}$alkyl substituted with one —$OC_{1-4}$alkyl;

and the pharmaceutically acceptable salts, and the solvates thereof.

The present invention relates in particular to compounds of Formula (I) as defined herein, and tautomers and stereoisomeric forms thereof, wherein $R^1$ is selected from the group of hydrogen; $C_{1-4}$alkyl; and $C_{1-4}$alkyl substituted with one or more fluoro substituents;

$R^2$ is selected from the group of $C_{1-4}$alkyl; $C_{1-4}$alkyl substituted with one or more fluoro substituents; $C_{3-6}$cycloalkyl; and Het$^1$;

Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;

X is N or CR$^9$;

$R^9$ is selected from hydrogen and halogen;

$R^3$ is selected from the group of hydrogen; halogen; cyano; $C_{3-6}$cycloalkyl; $C_{1-6}$alkyl; $C_{1-6}$alkyl substituted with one or more fluoro substituents; —$OC_{1-6}$alkyl; —$OC_{1-6}$alkyl substituted with one or more fluoro substituents; and $C_{1-6}$alkyl substituted with one substituent selected from —NR$^{3a}$R$^{3b}$ and —$OC_{1-4}$alkyl;

R$^{3a}$ and R$^{3b}$ are each independently selected from hydrogen and $C_{1-4}$alkyl;

$R^4$ is hydrogen;

$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of —NR$^{5a}$R$^{5b}$, and —$OC_{1-4}$alkyl;

R$^{5a}$ and R$^{5b}$ are each independently selected from the group of hydrogen and $C_{1-4}$alkyl;

$R^6$ is selected from the group of hydrogen; Het$^2$; $R^8$; $C_{1-6}$alkyl optionally substituted with one Het$^3$; and $C_{2-6}$alkyl substituted with one or more substituents independently selected from the group of fluoro, —NR$^{6a}$R$^{6b}$, and —OR$^{6c}$, R$^{6a}$, R$^{6b}$ and R$^{6c}$ are each independently selected from hydrogen and $C_{1-6}$alkyl;

Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

$R^8$ is $C_{3-6}$cycloalkyl optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$R^7$ is selected from the group of hydrogen, $C_{1-6}$alkyl, $C_{3-6}$cycloalkyl and $C_{1-4}$alkyl substituted with one —$OC_{1-4}$alkyl;

and the pharmaceutically acceptable salts, and the solvates thereof.

The present invention relates in particular to compounds of Formula (I) as defined herein, and tautomers and stereoisomeric forms thereof, wherein $R^1$ is selected from the group of hydrogen; $C_{1-4}$alkyl; and $C_{1-4}$alkyl substituted with one or more fluoro substituents;

$R^2$ is selected from the group of hydrogen; $C_{1-4}$alkyl; $C_{1-4}$alkyl substituted with one or more fluoro substituents; $C_{3-6}$cycloalkyl; and Het$^1$;

or $R^1$ and $R^2$ together with the carbon atom to which they are attached form a $C_{3-6}$cycloalkyl;

Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;

X is N;

$R^3$ is selected from the group of hydrogen; halogen; cyano; $C_{3-6}$cycloalkyl; $C_{1-6}$alkyl;

Het$^4$; $C_{1-6}$alkyl substituted with one or more fluoro substituents; —$OC_{1-6}$alkyl; —$OC_{1-6}$alkyl substituted with one or more fluoro substituents; and $C_{1-6}$alkyl substituted with one substituent selected from —NR$^{3a}$R$^{3b}$ and —$OC_{1-4}$alkyl;

Het$^4$ is a heteroaryl selected from the group of piperidinyl, tetrahydropyranyl, pyrrolidinyl, tetrahydrofuranyl, azetidinyl, piperazinyl, morpholinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

R$^{3a}$ and R$^{3b}$ are each independently selected from hydrogen and $C_{1-4}$alkyl;

$R^4$ is hydrogen;

$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of —NR$^{5a}$R$^{5b}$, —$OC_{1-4}$alkyl, and Het$^5$;

R$^{5a}$ and R$^{5b}$ are each independently selected from the group of hydrogen and $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

$R^6$ is selected from the group of hydrogen; Het$^2$; $R^8$; $C_{1-6}$alkyl optionally substituted with one Het$^3$; and $C_{2-6}$alkyl substituted with one or more substituents independently selected from the group of fluoro, —$NR^{6a}R^{6b}$, and —$OR^{6c}$, $R^{6a}$, $R^{6b}$ and $R^{6c}$ are each independently selected from hydrogen and $C_{1-6}$alkyl;

Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

$R^8$ is $C_{3-6}$cycloalkyl optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$R^7$ is selected from the group of hydrogen, $C_{1-6}$alkyl, $C_{3-6}$cycloalkyl and $C_{1-4}$alkyl substituted with one —$OC_{1-4}$alkyl;

and the pharmaceutically acceptable salts, and the solvates thereof.

The present invention relates in particular to compounds of Formula (I) as defined herein, and tautomers and stereoisomeric forms thereof, wherein $R^1$ is selected from the group of hydrogen; $C_{1-4}$alkyl; and $C_{1-4}$alkyl substituted with one or more fluoro substituents;

$R^2$ is selected from the group of hydrogen; $C_{1-4}$alkyl; $C_{1-4}$alkyl substituted with one or more fluoro substituents; $C_{3-6}$cycloalkyl; and Het$^1$;

or $R^1$ and $R^2$ together with the carbon atom to which they are attached form a $C_{3-6}$cycloalkyl;

Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;

X is $CR^9$;

$R^9$ is selected from hydrogen and halogen;

$R^3$ is selected from the group of hydrogen; halogen; cyano; $C_{3-6}$cycloalkyl; $C_{1-6}$alkyl;

Het$^4$; $C_{1-6}$alkyl substituted with one or more fluoro substituents; —$OC_{1-6}$alkyl; —$OC_{1-6}$alkyl substituted with one or more fluoro substituents; and $C_{1-6}$alkyl substituted with one substituent selected from —$NR^{3a}R^{3b}$ and —$OC_{1-4}$alkyl;

Het$^4$ is a heteroaryl selected from the group of piperidinyl, tetrahydropyranyl, pyrrolidinyl, tetrahydrofuranyl, azetidinyl, piperazinyl, morpholinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

$R^{3a}$ and $R^{3b}$ are each independently selected from hydrogen and $C_{1-4}$alkyl;

$R^4$ is hydrogen;

$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of —$NR^{5a}R^{5b}$, —$OC_{1-4}$alkyl, and Het$^5$;

$R^{5a}$ and $R^{5b}$ are each independently selected from the group of hydrogen and $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl and $C_{1-4}$alkyl substituted with one or more fluoro substituents;

$R^6$ is selected from the group of hydrogen; Het$^2$; $R^8$; $C_{1-6}$alkyl optionally substituted with one Het$^3$; and $C_{2-6}$alkyl substituted with one or more substituents independently selected from the group of fluoro, —$NR^{6a}R^{6b}$, and —$OR^{6c}$, $R^{6a}$, $R^{6b}$ and $R^{6c}$ are each independently selected from hydrogen and $C_{1-6}$alkyl;

Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, $C_{1-4}$alkyl substituted with one $C_{3-6}$cycloalkyl, and $C_{1-4}$alkyl substituted with one or more fluoro substituents;

$R^8$ is $C_{3-6}$cycloalkyl optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$R^7$ is selected from the group of hydrogen, $C_{1-6}$alkyl, $C_{3-6}$cycloalkyl and $C_{1-4}$alkyl substituted with one —$OC_{1-4}$alkyl;

and the pharmaceutically acceptable salts, and the solvates thereof.

The present invention relates in particular to compounds of Formula (I) as defined herein, and tautomers and stereoisomeric forms thereof, wherein $R^1$ is $C_{1-4}$alkyl;

$R^2$ is selected from the group of $C_{1-4}$alkyl; and $C_{3-6}$cycloalkyl;

X is N or $CR^9$;
$R^9$ is halogen; in particular fluoro;
$R^3$ is hydrogen;
$R^4$ is hydrogen;
$R^5$ is hydrogen;
$R^6$ is selected from the group of $Het^2$; and $C_{2-6}$alkyl substituted with one —$OR^{6c}$;
$R^{6c}$ is $C_{1-6}$alkyl;
$Het^2$ is a heterocyclyl, bound through any available carbon atom, selected from the group of pyrrolidinyl, and oxetanyl, each of which may be optionally substituted with one or two substituents independently selected from $C_{1-4}$alkyl, $C_{3-6}$cycloalkyl, and
$C_{1-4}$alkyl substituted with one $C_{3-6}$cycloalkyl;
$R^7$ is selected from the group of $C_{1-6}$alkyl, and $C_{3-6}$cycloalkyl;
and the pharmaceutically acceptable salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^1$ is $C_{1-4}$alkyl;
(b) $R^2$ is selected from the group of $C_{1-4}$alkyl; and $C_{3-6}$cycloalkyl;
(c) X is N or $CR^9$;
(d) $R^9$ is halogen; in particular fluoro;
(e) $R^3$ is hydrogen;
(f) $R^4$ is hydrogen;
(g) $R^5$ is hydrogen;
(h) $R^6$ is selected from the group of $Het^2$; and $C_{2-6}$alkyl substituted with one —$OR^{6c}$;
(i) $R^{6c}$ is $C_{1-6}$alkyl;
(j) $Het^2$ is a heterocyclyl, bound through any available carbon atom, selected from the group of pyrrolidinyl, and oxetanyl, each of which may be optionally substituted with one or two substituents independently selected from $C_{1-4}$alkyl, $C_{3-6}$cycloalkyl, and $C_{1-4}$alkyl substituted with one $C_{3-6}$cycloalkyl;
(k) $R^7$ is selected from the group of $C_{1-6}$alkyl, and $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein
$R^1$ is selected from the group of hydrogen $C_{1-4}$alkyl; and $C_{1-4}$alkyl substituted with one or more fluoro substituents;
$R^2$ is selected from the group of $C_{1-4}$alkyl; $C_{1-4}$alkyl substituted with one or more fluoro substituents; $C_{3-6}$cycloalkyl; and $Het^1$.

In an embodiment, the present invention relates to those compounds of Formula (I) and the pharmaceutically acceptable addition salts, and the solvates thereof, or any subgroup thereof as mentioned in any of the other embodiments, wherein
$R^1$ is selected from the group of $C_{1-4}$alkyl;
$R^2$ is selected from the group of $C_{1-4}$alkyl; $C_{1-4}$alkyl substituted with one or more fluoro substituents; $C_{3-6}$cycloalkyl; and $Het^1$.

In an embodiment, the present invention relates to those compounds of Formula (I) and the pharmaceutically acceptable addition salts, and the solvates thereof, or any subgroup thereof as mentioned in any of the other embodiments, wherein $R^1$ is selected from the group of $C_{1-4}$alkyl;
$R^2$ is selected from the group of $C_{1-4}$alkyl; $C_{1-4}$alkyl substituted with one or more fluoro substituents; $C_{3-6}$cycloalkyl; and $Het^1$;
or $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein
$Het^1$ is a heteroaryl selected from the group of thienyl, thiazolyl, pyrrolyl, oxazolyl, oxadiazolyl, pyrazolyl, imidazolyl, isoxazolyl, and isothiazolyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein X is N.

In an embodiment, the present invention relates to those compounds of Formula (I) and the pharmaceutically acceptable addition salts, and the solvates thereof, or any subgroup thereof as mentioned in any of the other embodiments, wherein X is N or CF.

In an embodiment, the present invention relates to those compounds of Formula (I) and the pharmaceutically acceptable addition salts, and the solvates thereof, or any subgroup thereof as mentioned in any of the other embodiments, wherein X is $CR^9$.

In an embodiment, the present invention relates to those compounds of Formula (I) and the pharmaceutically acceptable addition salts, and the solvates thereof, or any subgroup thereof as mentioned in any of the other embodiments, wherein X is CF.

In an embodiment, the present invention relates to those compounds of Formula (I) and the pharmaceutically acceptable addition salts, and the solvates thereof, or any subgroup thereof as mentioned in any of the other embodiments, wherein
$R^3$ is hydrogen; and $R^5$ is hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^6$ is $Het^2$.

In an embodiment, the present invention relates to those compounds of Formula (I) and the pharmaceutically acceptable addition salts, and the solvates thereof, or any subgroup thereof as mentioned in any of the other embodiments, wherein
$R^6$ is $Het^2$; and
$Het^2$ is a heterocyclyl, bound through any available carbon atom, selected from the group of pyrrolidinyl, and oxetanyl, each of which may be optionally substituted with one or two substituents independently selected from $C_{1-4}$alkyl, $C_{3-6}$cycloalkyl, and $C_{1-4}$alkyl substituted with one $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein
R$^6$ is C$_{2-6}$alkyl substituted with one —OR$^{6c}$; and
R$^{6c}$ is C$_{1-6}$alkyl.

In an embodiment, the present invention relates to those compounds of Formula (I) and the pharmaceutically acceptable addition salts, and the solvates thereof, or any subgroup thereof as mentioned in any of the other embodiments, wherein
R$^6$ is selected from the group of Het$^2$; and C$_{2-6}$alkyl substituted with one —OR$^{6c}$.

In an embodiment, the present invention relates to those compounds of Formula (I) and the pharmaceutically acceptable addition salts, and the solvates thereof, or any subgroup thereof as mentioned in any of the other embodiments, wherein
R$^6$ is selected from the group of Het$^2$; and C$_{2-6}$alkyl substituted with one —OR$^{6c}$;
R$^{6c}$ is C$_{1-6}$alkyl;
Het$^2$ is a heterocyclyl, bound through any available carbon atom, selected from the group of pyrrolidinyl, and oxetanyl, each of which may be optionally substituted with one or two substituents independently selected from C$_{1-4}$alkyl, C$_{3-6}$cycloalkyl, and C$_{1-4}$alkyl substituted with one C$_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein R$^{6c}$ is C$_{1-6}$alkyl; in particular methyl.

In an embodiment, the present invention relates to those compounds of Formula (I) and the pharmaceutically acceptable addition salts, and the solvates thereof, or any subgroup thereof as mentioned in any of the other embodiments, wherein Het$^3$ is a heterocyclyl, bound through any available carbon atom.

In an embodiment, the present invention relates to those compounds of Formula (I) and the pharmaceutically acceptable addition salts, and the solvates thereof, or any subgroup thereof as mentioned in any of the other embodiments, wherein
R$^6$ is selected from the group of

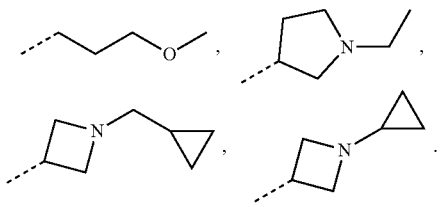

In an embodiment, the present invention relates to those compounds of Formula (I) and the pharmaceutically acceptable addition salts, and the solvates thereof, or any subgroup thereof as mentioned in any of the other embodiments, wherein
R$^6$ is selected from the group of

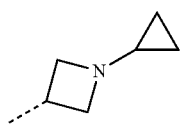

In an embodiment, the present invention relates to those compounds of Formula (I) and the pharmaceutically acceptable addition salts, and the solvates thereof, or any subgroup thereof as mentioned in any of the other embodiments, wherein R$^6$ is other than hydrogen.

Specific compounds according to the invention include:

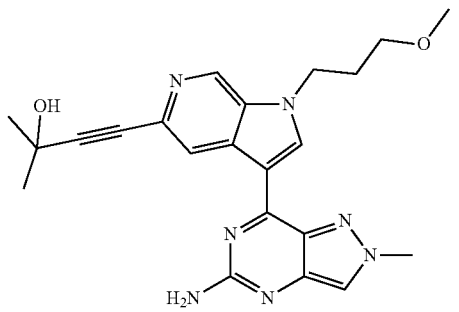

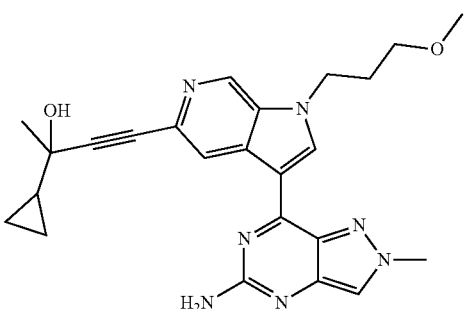

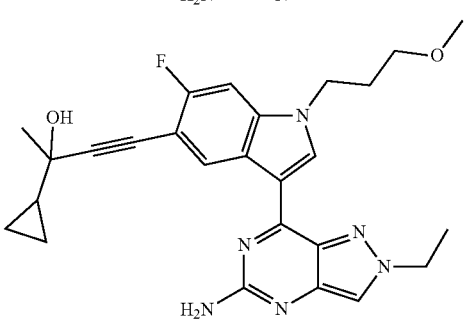

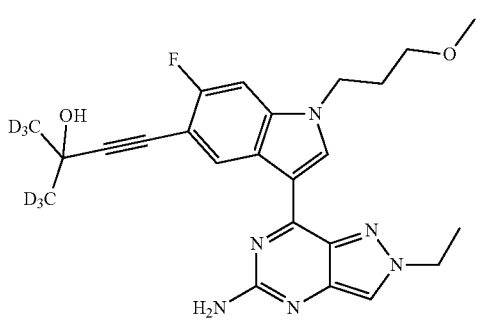

-continued

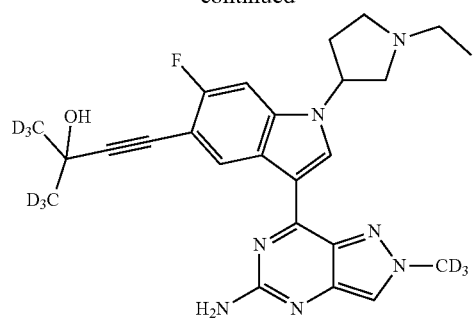
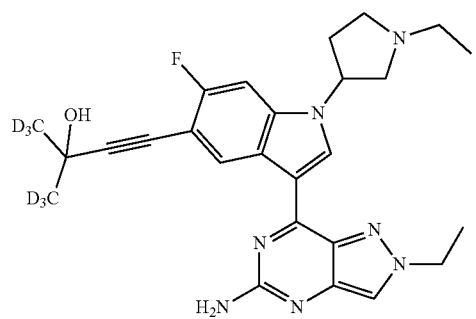
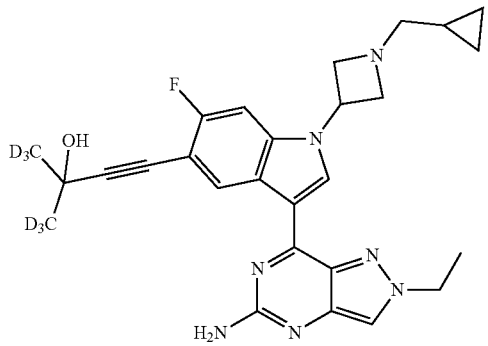
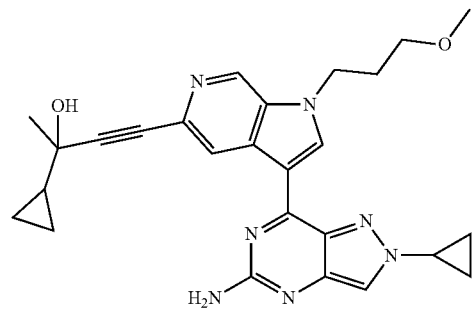
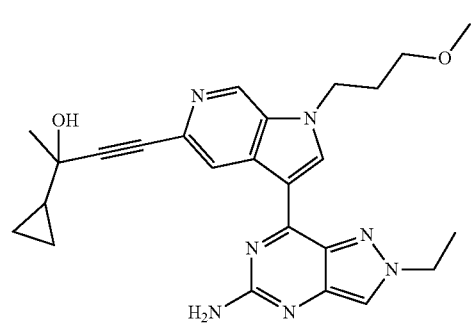

-continued

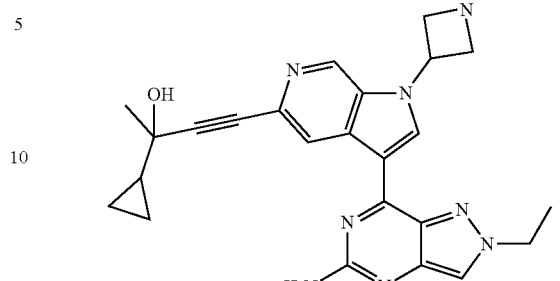
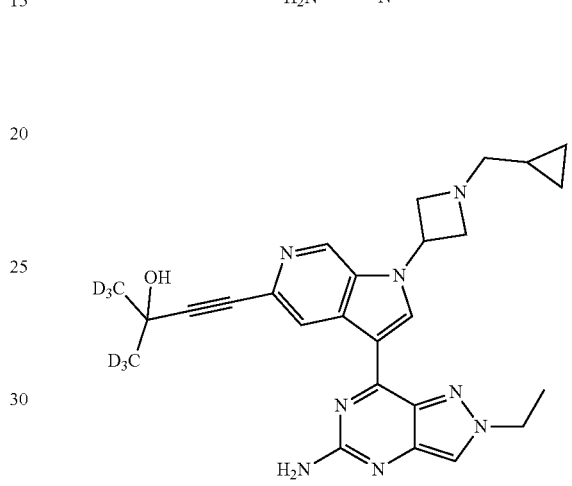
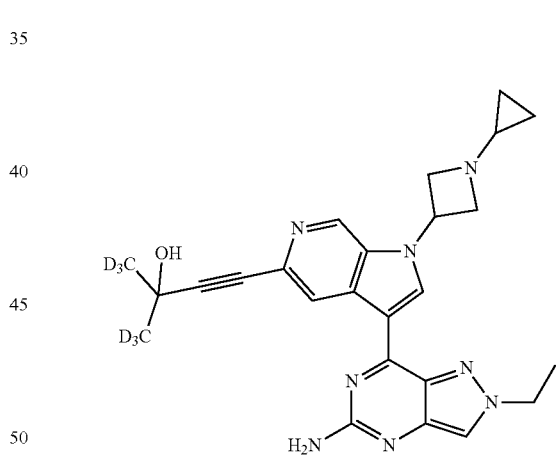

tautomers and stereoisomeric forms thereof, and the pharmaceutically acceptable salts, and the solvates thereof.

Methods of Synthesis

Compounds of Formula (I) can be prepared by methods known to those who are skilled in the art. The following schemes are only meant to represent examples of the invention and are in no way meant to be a limit of the invention.

Herein, the term 'DCM' means dichloromethane, 'DMF' means N,N-dimethylformamide, 'NMP' means N-methyl-2-pyrrolidone, 'Et$_3$N' means triethylamine, 'TFA' means trifluoroacetic acid and '[Ir(OMe)cod]$_2$' means (1,5-cyclooctadiene)(methoxy)iridium(I) dimer.

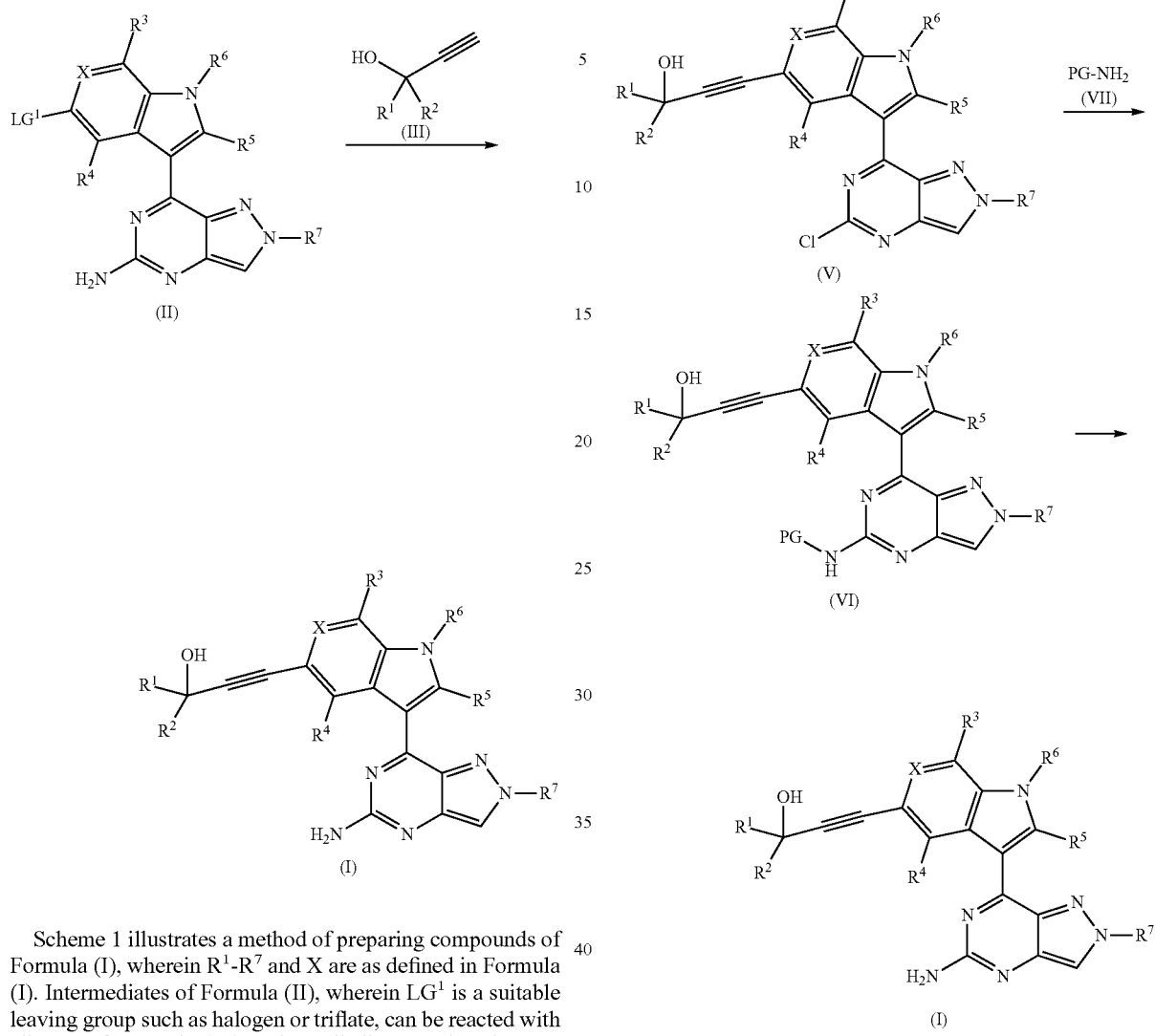

Scheme 1 illustrates a method of preparing compounds of Formula (I), wherein $R^1$-$R^7$ and X are as defined in Formula (I). Intermediates of Formula (II), wherein $LG^1$ is a suitable leaving group such as halogen or triflate, can be reacted with alkynes of Formula (III) under palladium-catalyzed Sonogashira coupling conditions, using for example Pd(PPh$_3$)$_4$, CuI and a base such as Et$_3$N in acetonitrile, with heating, to furnish compounds of Formula (I).

Alkynes of Formula (III), wherein $R^1$ and $R^2$ are as defined in Formula (I), are commercially available or can be prepared by known methods.

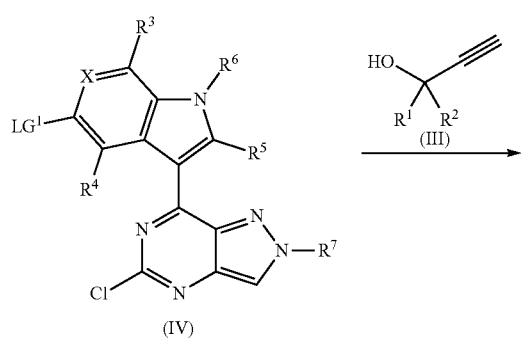

Scheme 2 illustrates a further method of preparing compounds of Formula (I), wherein $R^1$-$R^7$ and X are as defined in Formula (I). Intermediates of Formula (IV) can be reacted with alkynes of Formula (III) under palladium-catalysed Sonogashira coupling conditions, using for example Pd(PPh$_3$)$_4$, CuI and a base such as Et$_3$N in acetonitrile, with heating, to furnish intermediates of Formula (V). Büchwald-Hartwig amination of intermediates of Formula (V), using a suitably protected nitrogen species of Formula (VII) such as carbamic acid tert-butyl ester in an appropriate solvent such as 1,4-dioxane gives intermediates of Formula (VI). Removal of the protecting group under suitable conditions such as employing TFA in DCM furnishes compounds of Formula (I).

Additional compounds of Formula (I) can be prepared by elaboration of functional groups of compounds within the scope of this invention using standard chemistry. Such elaborations include, but are not limited to, hydrolysis, reduction, oxidation, alkylation, amidation and dehydration. Such transformations may in some instances require the use of protecting groups.

Scheme 3

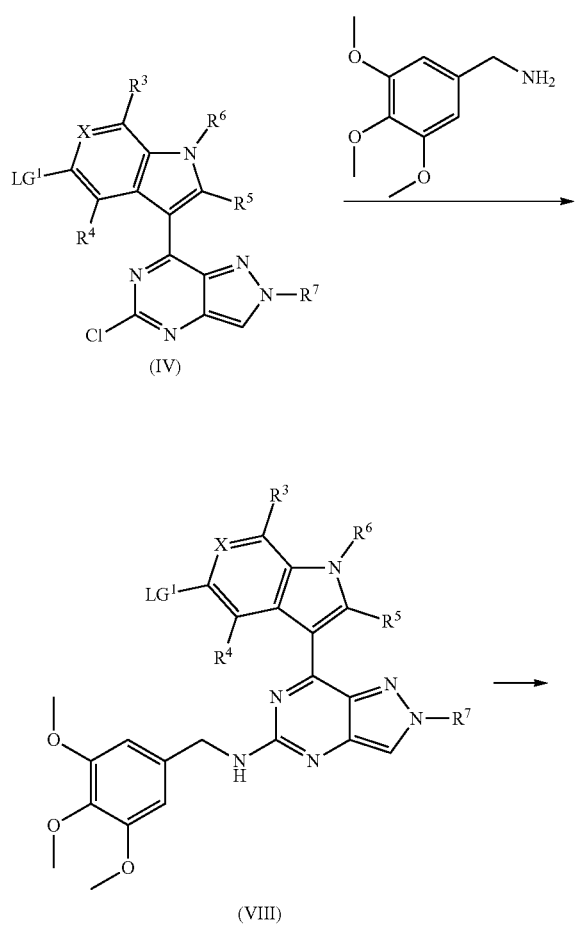

Scheme 4

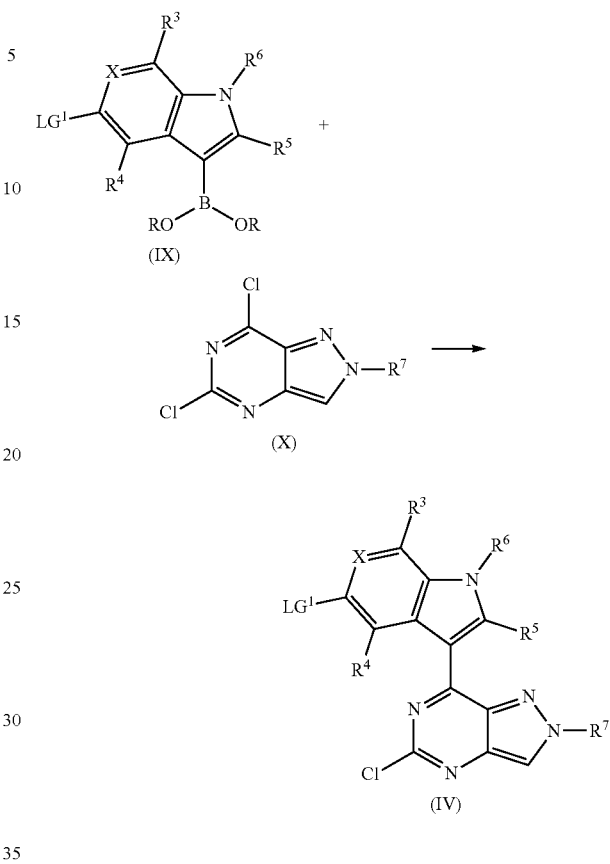

Scheme 4 illustrates a method of preparing intermediates of Formula (IV), wherein $R^3$-$R^7$ and X are as defined in Formula (I) and $LG^1$ is as defined above. Heating intermediates of Formula (X) with boronates of Formula (IX) under palladium-catalyzed Suzuki coupling conditions, using for example Pd(PPh$_3$)$_4$, Na$_2$CO$_3$ in water and 1,4-dioxane as solvent, yields intermediates of Formula (IV).

Intermediates of Formula (X), wherein $R^7$ is as defined in Formula (I), are commercially available or can be prepared by known methods (Baraldia et al. Bioorg. Med. Chem. 2012, 20, 1046-1059).

Scheme 3 illustrates a method of preparing intermediates of Formula (II), wherein $R^3$-$R^7$ and X are as defined in Formula (I) and $LG^1$ is as defined above. Intermediates of Formula (IV) can be reacted with 3,4,5-trimethoxybenzylamine under basic conditions, for example employing pyridine in a suitable solvent such as NMP with heating, to yield benzylamines of Formula (VIII). The 3,4,5-trimethoxybenzyl group can be removed under suitable conditions, for example employing TFA with heating to furnish intermediates of Formula (II).

Scheme 5

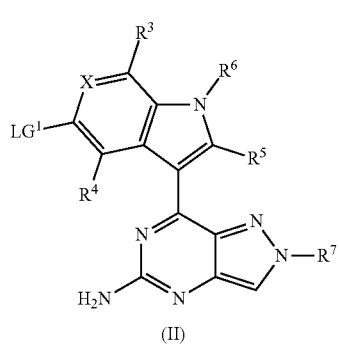

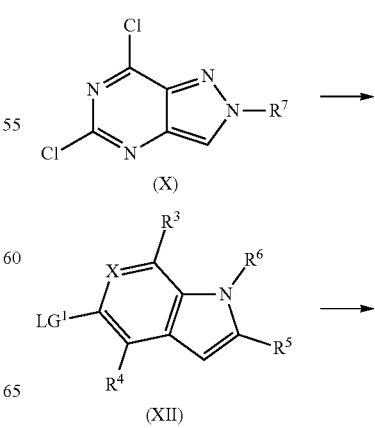

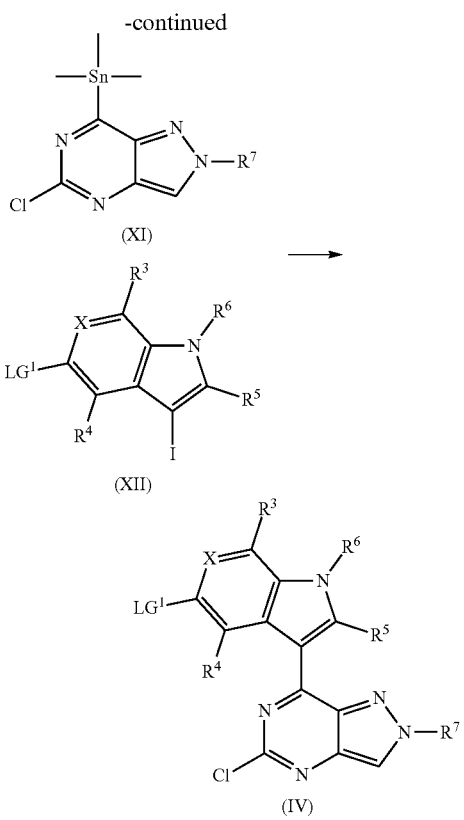

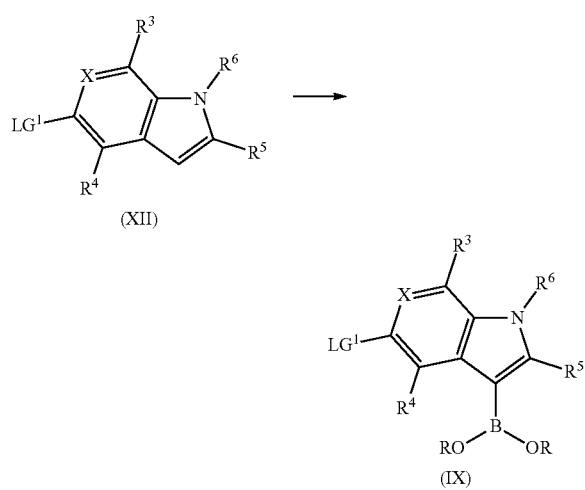

Scheme 5 illustrates a further method for preparing intermediates of Formula (IV), wherein $R^3$-$R^7$ and X are as defined in Formula (I) and $LG^1$ is as defined above. Heating intermediates of Formula (X) with hexamethylditin in the presence of $Pd(PPh_3)_4$ yields intermediates of Formula (XI). Intermediates of Formula (XIII) can be prepared by treating intermediates of Formula (XII) with a mixture of iodine and potassium hydroxide in a suitable solvent such as DMF. Heating intermediates of Formula (XI) and (XIII) under Stille-type coupling conditions, using for example $Pd(PPh_3)_4$ and copper(I)-thiophene-2-carboxylate in 1,4-dioxane as a solvent, yields intermediates of Formula (IV).

Scheme 6 illustrates a method of preparing intermediates of Formula (IX), wherein $R^3$-$R^6$ and X are as defined in Formula (I) and $LG^1$ is as defined above. Heating of intermediates of Formula (XII) with an appropriate borane species, such as 4,4,5,5-tetramethyl-1,3,2-dioxaborolane, under Iridium-catalyzed conditions using for example [Ir(OMe)cod]$_2$ with an appropriate ligand, such as 4,4-di-tert-butyl-2,2-dipyridyl, and cyclohexane as solvent yields boronates of Formula (IX).

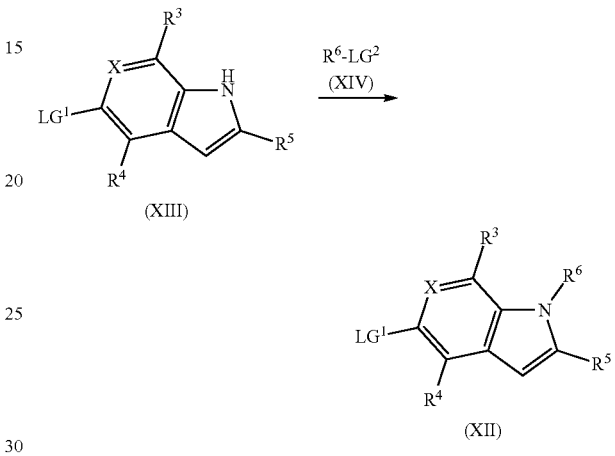

Scheme 7 illustrates a method of preparing intermediates of Formula (XII), wherein $R^3$-$R^6$ and X are as defined in Formula (I) and $LG^1$ is as defined above. Treatment of intermediates of Formula (XIII) with a suitable electrophile under basic conditions, such as $R^6$-$LG^2$ (XIV), wherein $LG^2$ is a leaving group such as halogen, mesylate or triflate, using for instance, cesium carbonate in DMF under heating, yields intermediates of Formula (XII).

Intermediates of Formula (XIII) and (XIV), wherein $R^3$-$R^6$ and X is as defined in Formula (I), and $LG^1$ and $LG^2$ are as defined above, are commercially available or can be prepared by known methods (Merour et al. Tet. 2013, 69, 4767-4834; Tabera et al. Tet. 2011 67, 7195-7210).

It will be appreciated that where appropriate functional groups exist, compounds of various Formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Compounds of the invention may be prepared from commercially available starting materials using the general methods illustrated herein.

Pharmacology

It has been found that the compounds of the present invention inhibit NF-κB-inducing kinase (NIK—also known as MAP3K14). The compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma, for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), or a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), or a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase. Also, the present invention relates to the use of a compound of Formula (I), or a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), or a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), or a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), or a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), or a tautomer or a stereoisomeric form thereof, or a pharmaceutically acceptable salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), or a tautomer or a stereoisomeric form thereof, or a pharmaceutically acceptable salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), or a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoïden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, MLN.41 or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-737;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification.

Herein, the term 'Cs$_2$CO$_3$' means cesium carbonate, 'Et$_3$N' means triethylamine, 'DCM' means dichloromethane, 'BEH' means bridged ethylsiloxane/silica hybrid, 'DIPEA' means diisopropylethylamine, 'DMAP' means N,N-dimethylpyridin-4-amine, 'DMF' means N,N-dimethylformamide, 'Celite®' means diatomaceous earth, 'DMSO' means dimethylsulfoxide, 'UPLC' means ultra performance liquid chromatography, 'LC' means liquid chromatography, 'EtOAc' means ethyl acetate, 'HPLC' means high performance liquid chromatography, 'LCMS' means liquid chromatography/mass spectrometry, 'MeCN' means acetonitrile, 'MeOH' means methanol, 'Na$_2$SO$_4$' means sodium sulfate, 'NMP' means N-methylpyrrolidinone, 'R$_t$' means retention time, 'ISOLUTE® SCX-2 SPE' means ISOLUTE® silica propylsulfonic acid strong cation exchange column, 'TBAF' means tetrabutylammonium fluoride, 'TFA' means trifluoroacetic acid and 'THF' means tetrahydrofuran, 'Et$_2$O' means diethyl ether, 'Xantphos' means [(4,5-bis(diphenylphosphino)-9,9-dimethylxanthene)-2-(2'-amino-1,1'-biphenyl)]palladium(II) methanesulfonate.

In the structures of the intermediates and the compounds of the present invention, deuterium ($^2H$) is represented by the chemical symbol D.

When in the Examples below, intermediates or compounds were prepared according to the reaction protocol of a fully described Example, this means that the intermediate or compound was prepared by an analogous reaction protocol (but not necessarily identical) as the Example referred to.

Preparation of Intermediates

Example A1 a) Preparation of Intermediate 1

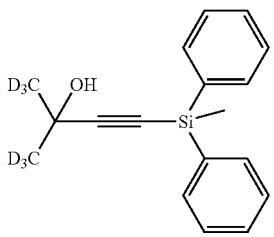 [SMILES: [2H]C([2H])([2H])C(O)(C#C[Si](C)(c1ccccc1)c1ccccc1)C([2H])([2H])[2H]]

A stirred solution of (methyldiphenylsilyl)acetylene (4.95 ml, 22.5 mmol) in anhydrous THF (80 ml) under an argon atmosphere at −78° C. was treated with a 1.6 M solution of n-butyllithium in hexanes (15.5 ml, 24.8 mmol) maintaining the temperature below −70° C. After 1 hour, the mixture was treated with acetone-$d_6$ (1.95 ml, 27.0 mmol) and the resulting mixture stirred at 0° C. for 1.5 hours. The mixture was quenched by the addition of water and partitioned between water and EtOAc. The organic phase was washed with brine, dried over $Na_2SO_4$ and concentrated in vacuo. The residue was purified by column chromatography on silica gel, eluting with a mixture of EtOAc and cyclohexane (0:1 to 2:3 by volume), to afford the desired product as a colourless oil (6.31 g, 98%).

Example A2 a) Preparation of Intermediate 2

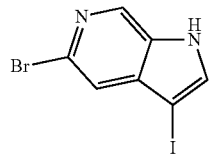 [SMILES: Brc1cc2c(I)c[nH]c2cn1]

A stirred solution of 5-bromo-1H-pyrrolo[2,3-c]pyridine (2.22 g, 11.3 mmol) in DMF (30 ml) at ambient temperature was treated with potassium hydroxide (2.53 g, 45.1 mmol). After 10 minutes, iodine (3.15 g, 12.4 mmol) was added and the resulting mixture was stirred for 2 hours. The mixture was diluted with water and extracted with EtOAc. The combined organic extracts were washed with brine, dried over $Na_2SO_4$ and concentrated in vacuo. The residue was triturated with water to afford the desired product as an orange solid (3.39 g, 93%).

LCMS (Method C): $R_t$=3.14 min, m/z $[M+H]^+$=323/325.

b) Preparation of Intermediate 3

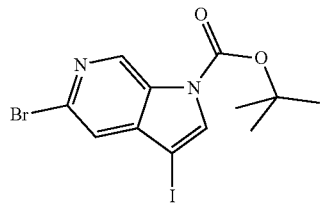 [SMILES: CC(C)(C)OC(=O)n1cc(I)c2cc(Br)ncc21]

A stirred suspension of intermediate 2 (3.39 g, 10.5 mmol) in DCM (60 ml) at 0° C. was treated sequentially with DMAP (0.128 g, 1.05 mmol), DIPEA (3.66 ml, 21.0 mmol) and di-tert-butyldicarbonate (3.44 g, 15.7 mmol). The resulting mixture was warmed to ambient temperature and stirred for 1 hour. The mixture was concentrated in vacuo and trituration of the residue with water afforded the desired product as a pale yellow solid (4.24 g, 96%).

LCMS (Method C): $R_t$=4.58 min, m/z $[M+H]^+$=423/425.

c) Preparation of Intermediate 4

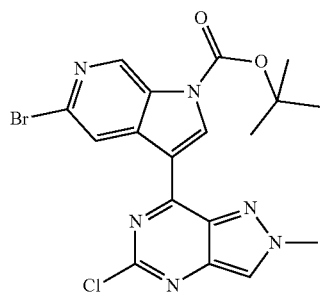 [SMILES: Cn1cc2nc(Cl)nc(-c3cn(C(=O)OC(C)(C)C)c4cnc(Br)cc34)c2n1]

A degassed mixture of 5,7-dichloro-2-methyl-2H-pyrazolo[4,3-d]pyrimidine (0.10 g, 0.49 mmol), hexamethylditin (0.18 g, 0.54 mmol), tetrakis(triphenylphosphine)palladium(0) (0.03 g, 0.024 mmol) and 1,4-dioxane (2.0 ml) under an argon atmosphere was heated at 80° C. for 1 hour. The reaction mixture was cooled to ambient temperature, treated with a degassed mixture of tetrakis(triphenylphosphine)palladium(0) (0.03 g, 0.024 mmol), intermediate 3(0.21 g, 0.49 mmol), copper thiophene carboxylate (0.009 g, 0.05 mmol) and 1,4-dioxane (2.0 ml), and the resulting mixture was heated at 80° C. for 18 hours. The mixture was cooled to ambient temperature and concentrated in vacuo. Trituration of the residue with $Et_2O$ afforded the desired compound as a yellow solid (0.14 g, 62%).

LCMS (Method C): $R_t$=4.59 min, m/z $[M+H]^+$=463/465/467.

d) Preparation of Intermediate 5

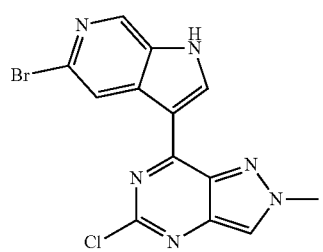 [SMILES: Cn1cc2nc(Cl)nc(-c3c[nH]c4cnc(Br)cc34)c2n1]

A stirred solution of intermediate 4 (0.74 g, 1.59 mmol) in DCM (10 ml) under a nitrogen atmosphere at 5° C. was treated with TFA (3.0 ml, 39.0 mmol), and the resulting mixture was stirred at ambient temperature for 3 hours. The mixture was concentrated in vacuo and trituration of the residue with Et$_2$O afforded the desired product as a pale yellow solid (0.80 g, 100%).

LCMS (Method C): R$_t$=3.12 min, m/z [M+H]$^+$=363/365/367.

e) Preparation of Intermediate 6

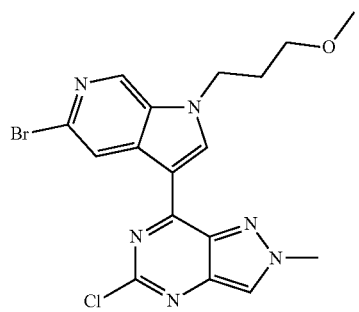 [SMILES: COCCCn1cc(-c2nc(Cl)nc3cn(C)nc23)c2cc(Br)ncc21]

A stirred mixture of intermediate 5 (0.40 g, 1.1 mmol), 1-bromo-3-methoxypropane (0.08 ml, 0.55 mmol), Cs$_2$CO$_3$ (0.72 g, 2.20 mmol) and DMF (4.0 ml) was heated by microwave irradiation at 110° C. for 1 hour. The mixture was cooled to ambient temperature and concentrated in vacuo. Trituration of the residue with Et$_2$O afforded a solid. The solid was collected by filtration and washed sequentially with water and acetone to afford the desired product as a brown solid (0.32 g, 66%).

LCMS (Method B): R$_t$=3.54 min, m/z [M+H]$^+$=435/437/439.

f) Preparation of Intermediate 7

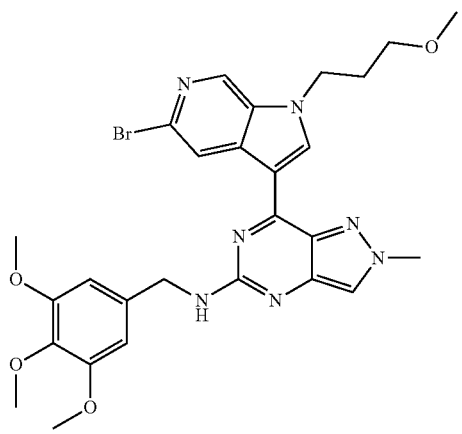 [SMILES: COCCCn1cc(-c2nc(NCc3cc(OC)c(OC)c(OC)c3)nc3cn(C)nc23)c2cc(Br)ncc21]

A stirred mixture of intermediate 6 (0.28 g, 0.64 mmol), 3,4,5-trimethoxybenzylamine (0.63 g, 3.19 mmol), pyridine (0.51 g, 6.32 mmol) and NMP (4.0 ml) was heated by microwave irradiation at 185° C. for 2 hours. The mixture was cooled to ambient temperature and purified by ISO-LUTE® SCX-2 SPE column eluting with a mixture of MeOH and 2.0 M ammonia solution in MeOH (1:0 to 0:1 by volume). Further purification by column chromatography on silica gel, eluting with a mixture of MeOH and DCM (0:1 to 1:9 by volume), afforded the desired product as a pale yellow solid (0.15 g, 39%).

LCMS (Method B): R$_t$=2.45 min, m/z [M+H]$^+$=596/598.

g) Preparation of Intermediate 8

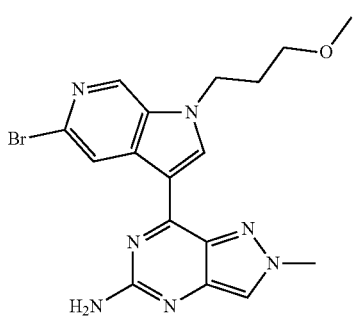 [SMILES: COCCCn1cc(-c2nc(N)nc3cn(C)nc23)c2cc(Br)ncc21]

A stirred mixture of intermediate 7 (0.14 g, 0.24 mmol) and TFA (1.0 ml, 13.1 mmol) under a nitrogen atmosphere was heated at reflux for 72 hours. The mixture was cooled to ambient temperature and concentrated in vacuo. The residue was purified by ISOLUTE® SCX-2 SPE column eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (0:1 to 1:9 by volume), followed by trituration with Et$_2$O afforded the desired product as a brown solid (0.04 g, 45%).

LCMS (Method B): R$_t$=1.79 and 1.98 min, m/z [M+H]$^+$=416/418.

Example A3 a) Preparation of Intermediate 9

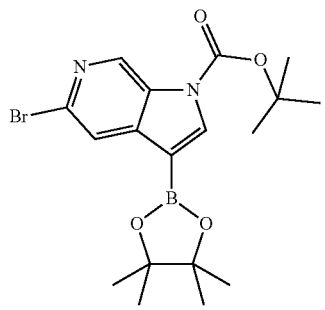 [SMILES: CC(C)(C)OC(=O)n1cc(B2OC(C)(C)C(C)(C)O2)c2cc(Br)ncc21]

A degassed mixture of 5-bromo-pyrrolo[2,3-c]pyridine-1-carboxylic acid tert-butyl ester (50.0 g, 168 mmol), 4,4,-di-tert-butyl-2,2-dipyridyl (0.90 g, 3.37 mmol) and cyclohexane (500 ml) under an argon atmosphere at ambient temperature was treated sequentially with di-μ-methoxobis (1,5-cyclooctadiene)diiridium (1.12 g, 1.68 mmol) and 4,4,5,5-tetramethyl-1,3,2-dioxaborolane (122 ml, 841 mmol), and the resulting mixture was stirred at 60° C. for 5 hours. The mixture was cooled to ambient temperature and concentrated in vacuo. The residue was purified by column chromatography on silica gel, eluting with a mixture of EtOAc and pentane (0:1 to 1:1 by volume), to afford the desired product as a white solid (50.0 g, 70%).

LCMS (Method B): R$_t$=4.78 min, m/z [M+H]$^+$=423/425.

b) Preparation of Intermediate 10

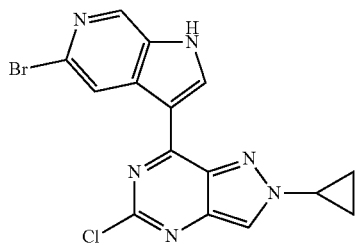 [SMILES: Clc1nc(-c2c[nH]c3cnc(Br)cc23)c2nn(C3CC3)cc2n1]

A degassed mixture of intermediate 9 (1.16 g, 2.75 mmol), 5,7-dichloro-2-cyclopropyl-2H-pyrazolo[4,3-d]pyrimidine (0.42 g, 1.83 mmol), tetrakis(triphenylphosphine) palladium (0.11 g, 0.09 mmol), sodium carbonate (0.58 mg, 5.5 mmol), 1,4-dioxane (9.0 ml) and water (3.0 ml) was stirred under an argon atmosphere at 100° C. for 5 hours. The mixture was cooled to ambient temperature and poured onto MeOH (30 ml). The resulting solid was collected by filtration and washed sequentially with water and Et₂O. The solid was treated with TFA (7.0 ml), and the resulting mixture stirred at ambient temperature for 1 hour. The mixture was concentrated in vacuo to afford the desired product (0.92 g, 100%).

LCMS (Method B): $R_t$=3.46 min, m/z [M+H]⁺=389/391/393.

c) Preparation of Intermediate 11

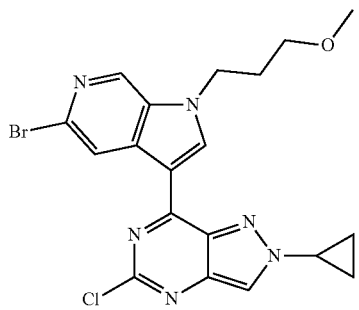 [SMILES: COCCCn1cc(-c2nc(Cl)nc3cn(C4CC4)nc23)c2cc(Br)ncc21]

A stirred mixture of intermediate 10 (0.92 g, 1.84 mmol), 1-bromo-3-methoxypropane (0.35 g, 2.29 mmol), Cs₂CO₃ (2.39 g, 7.33 mmol) and DMF (10 ml) was heated by microwave irradiation at 110° C. for 2.0 hours. The mixture was cooled to ambient temperature and partitioned between water and EtOAc. The organic phase was dried over Na₂SO₄ and concentrated in vacuo. Trituration of the residue with Et₂O afforded the desired product as a pale yellow solid (0.57 g, 67%).

LCMS (Method B): $R_t$=4.02 min, m/z [M+H]⁺=461/463/465.

d) Preparation of Intermediate 12

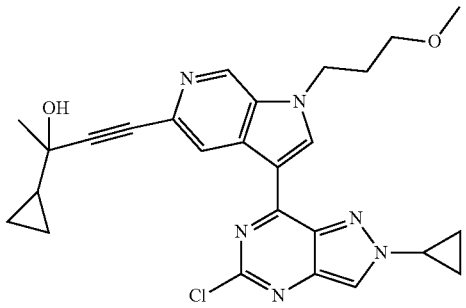 [SMILES: COCCCn1cc(-c2nc(Cl)nc3cn(C4CC4)nc23)c2cc(C#CC(C)(O)C3CC3)ncc21]

A stirred mixture of intermediate 11 (0.55 g, 1.19 mmol), 2-cyclopropyl-but-3-yn-2-ol (0.16 g, 1.43 mmol), tetrakis(triphenylphosphine) palladium (0.14 g, 0.12 mmol), copper (I) iodide (13.3 mg, 0.07 mmol), Et₃N (0.60 ml, 5.95 mmol) and MeCN (8.0 ml) was heated by microwave irradiation at 90° C. for 1 hour. The mixture was cooled to ambient temperature and concentrated in vacuo. The residue was purified by column chromatography on silica gel, eluting with a mixture of MeOH and DCM (0:1 to 1:9 by volume), to afford the desired product as a pale yellow solid (0.22 g, 0.44 mmol).

LCMS (Method B): $R_t$=3.16 min, m/z [M+H]⁺=491/493.

Intermediate 13 was prepared by an analogous reaction protocol as intermediate 10 using the appropriate starting materials (Table 1).

TABLE 1

| Intermediate | Structure | Starting Materials | LCMS Data |
| --- | --- | --- | --- |
| 13 | 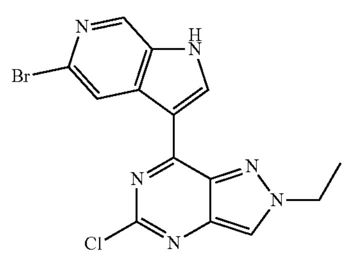 [SMILES: CCn1cc2nc(Cl)nc(-c3c[nH]c4cnc(Br)cc34)c2n1] | a) Intermediate 9<br>b) 5,7-Dichloro-2-ethyl-2H-pyrazolo[4,3-d]pyrimidine | $R_t$ = 3.35 min, m/z [M + H]⁺ = 377/379/381 (Method C) |

Intermediate 14 was prepared by an analogous reaction protocol as intermediate 11 using the appropriate starting materials (Table 2).

TABLE 2

| Intermediate | Structure | Starting Materials | LCMS Data |
| --- | --- | --- | --- |
| 14 | 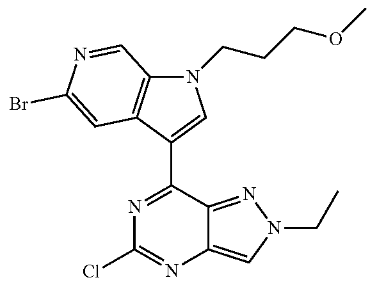 [SMILES: CCn1cc2nc(Cl)nc(-c3cn(CCCOC)c4cnc(Br)cc34)c2n1] | a) Intermediate 13<br>b) 1-Bromo-3-methoxypropane | $R_t$ = 3.80 min,<br>m/z [M + H]$^+$ = 449/451/453<br>(Method B) |

Intermediates 15 to 18 were prepared by an analogous reaction protocol as intermediate 12 using the appropriate starting materials (Table 3).

TABLE 3

| Intermediate | Structure | Starting Materials | LCMS Data |
| --- | --- | --- | --- |
| 15 | 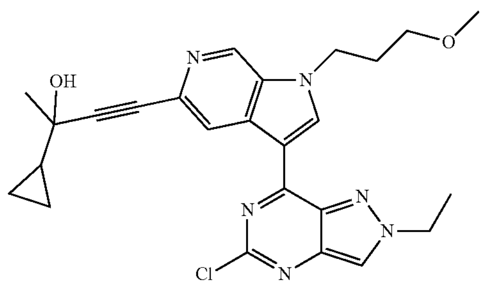 [SMILES: CCn1cc2nc(Cl)nc(-c3cn(CCCOC)c4cnc(C#CC(C)(O)C5CC5)cc34)c2n1] | a) Intermediate 14<br>b) 2-Cyclopropyl-but-3-yn-2-ol | $R_t$ = 3.03 min,<br>m/z [M + H]$^+$ = 479/481<br>(Method B) |
| 16 | 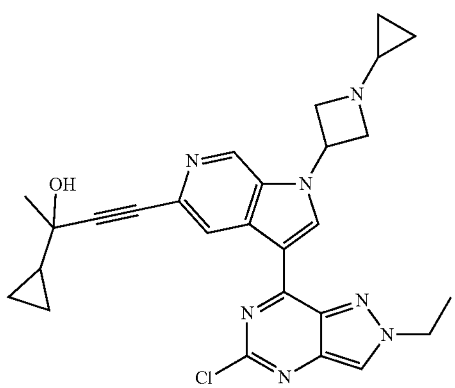 [SMILES: CCn1cc2nc(Cl)nc(-c3cn(C4CN(C5CC5)C4)c4cnc(C#CC(C)(O)C5CC5)cc34)c2n1] | a) Intermediate 36<br>b) 2-Cyclopropyl-but-3-yn-2-ol | $R_t$ = 2.36 min,<br>m/z [M + H]$^+$ = 502/504<br>(Method B) |
| 17 | 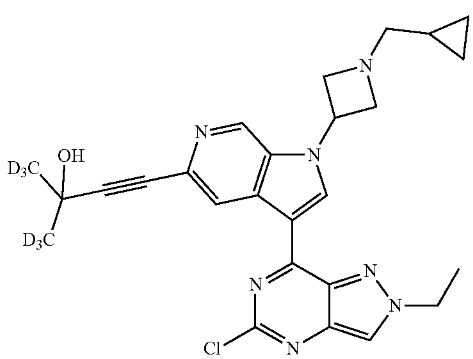 [SMILES: [2H]C([2H])([2H])C(O)(C#Cc1cc2c(-c3nc(Cl)nc4cn(CC)nc34)cn(C3CN(CC4CC4)C3)c2cn1)C([2H])([2H])[2H]] | a) Intermediate 43<br>b) 1,1,1-Trideutero-2-trideuteromethyl-3-butyn-2-ol | $R_t$ = 2.23 min,<br>m/z [M + H]$^+$ = 496/498<br>(Method C) |

TABLE 3-continued

| Intermediate | Structure | Starting Materials | LCMS Data |
|---|---|---|---|
| 18 | 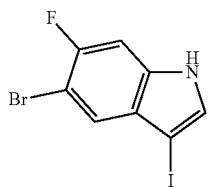 [SMILES: Fc1cc2[nH]cc(I)c2cc1Br] | a) Intermediate 36<br>b) 1,1,1-Trideutero-2-trideuteromethyl-3-butyn-2-ol | $R_t$ = 2.20 min,<br>m/z [M + H]$^+$ =<br>482/484<br>(Method C) |

Example A4 a) Preparation of Intermediate 19

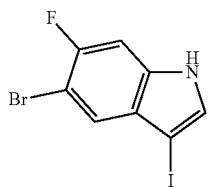 [SMILES: Fc1cc2[nH]cc(I)c2cc1Br]

A stirred solution of 5-bromo-6-fluoro-1H-indole (2.5 g, 11.7 mmol) in DMF (30 ml) at ambient temperature was treated with potassium hydroxide (2.5 g, 44.6 mmol). After 10 minutes, iodine (4.45 g, 17.5 mmol) was added and the resulting mixture was stirred for 18 hours. The mixture was diluted with water and extracted with EtOAc. The combined extracts were washed with 5% aqueous sodium metabisulfite solution and brine, dried over Na$_2$SO$_4$ and concentrated in vacuo. The residue was purified by column chromatography on silica gel, eluting with a mixture of EtOAc and cyclohexane (0:1 to 2:3 by volume), to afford the desired product as an off-white solid (1.88 g, 47%).

LCMS (Method B): $R_t$=3.94 min, m/z [M−H]$^{31}$=338/340.

b) Preparation of Intermediate 20

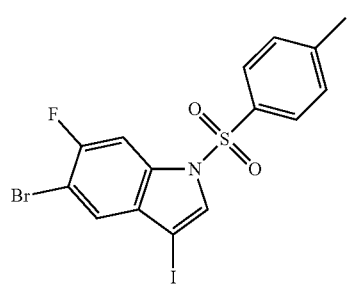 [SMILES: Cc1ccc(S(=O)(=O)n2cc(I)c3cc(Br)c(F)cc32)cc1]

A mixture of intermediate 19 (29.4 g, 86.7 mmol), 4-methylbenzenesulfonyl chloride (16.5 g, 86.7 mmol), sodium hydroxide (6.8 g, 152 mmol), benzyltriethylammonium chloride (1.64 g, 8.67 mmol) and anhydrous DCM (52 ml) was stirred at 0° C. for 1 hour and then at ambient temperature for 2 hours. The mixture was partitioned between water and EtOAc. The organic phase was washed with brine, dried over Na$_2$SO$_4$ and concentrated in vacuo. The residue was purified by crystallisation from a mixture of EtOAc and petroleum ether (1:1 by volume) to afford the desired product as a white solid (20 g, 47%).

Example A5 a) Preparation of Intermediate 21

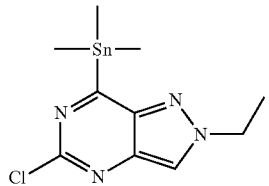 [SMILES: CCn1cc2nc(Cl)n[c]([Sn]([CH3])([CH3])[CH3])c2n1]

A degassed mixture of 5,7-dichloro-2-ethyl-2H-pyrazolo[4,3-d]pyrimidine (0.10 g, 0.46 mmol), hexamethylditin (0.30 g, 0.92 mmol), tetrakis(triphenylphosphine)palladium (0) (0.03 g, 0.023 mmol) and 1,4-dioxane (6.0 ml) under an argon atmosphere was heated at 80° C. for 7 hours. The mixture was cooled to ambient temperature, filtered through Celite® and the filtrate concentrated in vacuo to afford the desired product as a brown solid (0.17 g, 100%).

LCMS (Method B): $R_t$=3.76 min, m/z [M+H]$^+$=345/347.

b) Preparation of Intermediate 22

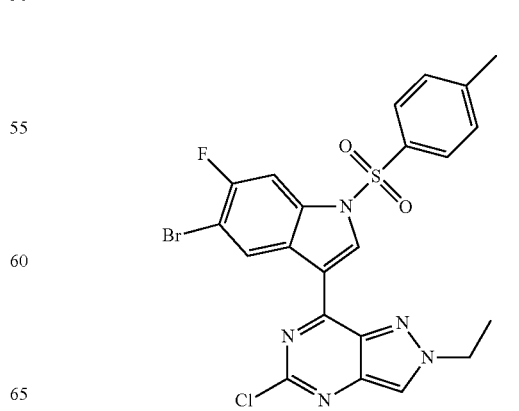

A degassed mixture of intermediate 20 (0.23 g, 0.47 mmol), intermediate 21 (0.16 g, 0.47 mmol), tetrakis(triphenylphosphine)palladium(0) (0.03 g, 0.023 mmol), copper thiophene carboxylate (0.009 g, 0.046 mmol) and 1,4-dioxane (3.0 ml) was heated at 85° C. for 18 hours. The mixture was cooled to ambient temperature and concentrated in vacuo. Trituration of the residue with Et$_2$O afforded the desired product as a light brown solid (0.26 g, 100%).

LCMS (Method B): R$_t$=4.98 min, m/z [M+H]$^+$=548/550/552.

c) Preparation of Intermediate 23

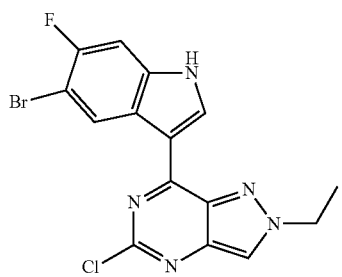 [SMILES: CCn1cc2nc(Cl)nc(-c3c[nH]c4cc(F)c(Br)cc34)c2n1]

A stirred solution of intermediate 22 (0.35 g, 0.64 mmol) in a mixture of THF (10 ml) and MeOH (30 ml) at ambient temperature was treated with sodium methoxide (25% wt. in MeOH, 1.46 ml, 6.4 mmol), and the resulting mixture was stirred for 45 minutes. The mixture was concentrated in vacuo and the residue partitioned between EtOAc and a saturated aqueous sodium hydrogen carbonate solution. The organic phase was washed with brine, dried over Na$_2$SO$_4$ and concentrated in vacuo. Trituration of the residue with Et$_2$O afforded the desired product as a yellow solid (0.21 g, 82%).

LCMS (Method B): R$_t$=3.95 min, m/z [M+H]$^+$=394/396/398.

d) Preparation of Intermediate 24

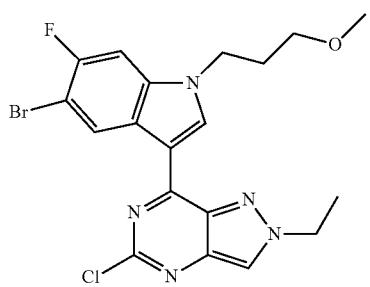 [SMILES: CCn1cc2nc(Cl)nc(-c3cn(CCCOC)c4cc(F)c(Br)cc34)c2n1]

A stirred solution of intermediate 23 (0.21 g, 0.53 mmol) in DMF (4.0 ml) at ambient temperature was treated with sodium hydride (60% in mineral oil, 0.023 g, 0.58 mmol). After 5 minutes, the mixture was treated with 1-bromo-3-methoxypropane (0.09 g, 0.58 mmol) and the resulting mixture was stirred at 50° C. for 2.0 hours. The mixture was cooled to ambient temperature and partitioned between EtOAc and brine. The organic phase was dried over Na$_2$SO$_4$ and concentrated in vacuo. Trituration of the residue with Et$_2$O afforded the desired product as a yellow solid (0.21 g, 88%).

LCMS (Method B): R$_t$=4.43 min, m/z [M+H]$^+$=466/468/470.

e) Preparation of Intermediate 25

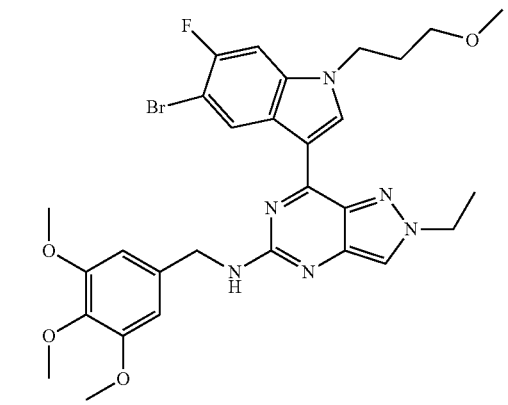 [SMILES: CCn1cc2nc(NCc3cc(OC)c(OC)c(OC)c3)nc(-c3cn(CCCOC)c4cc(F)c(Br)cc34)c2n1]

A stirred mixture of intermediate 24 (0.62 g, 1.32 mmol), 3,4,5-trimethoxybenzylamine (1.31 g, 6.62 mmol), pyridine (1.05 g, 13.2 mmol) and NMP (9.0 ml) was heated at 140° C. for 37 hours. The mixture was cooled to ambient temperature and concentrated in vacuo. The residue was purified by ISOLUTE® SCX-2 SPE column eluting with a mixture of MeOH and 2.0 M ammonia solution in MeOH (1:0 to 0:1 by volume). Further purification by column chromatography on silica gel, eluting with a mixture of 2.0 M ammonia solution in MeOH and DCM (0:1 to 1:19 by volume), afforded the desired product as a pale yellow oil (0.83 g, 100%).

LCMS (Method C): R$_t$=2.94 min, m/z [M+H]$^+$=627/629.

f) Preparation of Intermediate 26

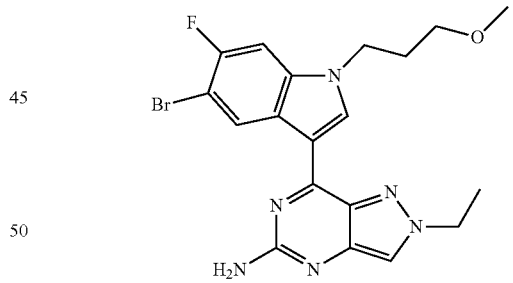

A stirred mixture of intermediate 25 (0.83 g, 1.23 mmol) and TFA (3.5 ml, 45.8 mmol) under a nitrogen atmosphere was heated at 75° C. for 2 hours. The mixture was cooled to ambient temperature and concentrated in vacuo. The residue was purified by ISOLUTE® SCX-2 SPE column, eluting with a mixture of MeOH and 2.0 M ammonia solution in MeOH (1:0 to 0:1 by volume), to afford the desired product as a yellow foam (0.53 g, 90%).

LCMS (Method B): R$_t$=2.62 min, m/z [M+H]$^+$=447/449.

Intermediate 27 was prepared by an analogous reaction protocol as intermediate 21 using the appropriate starting material (Table 4).

TABLE 4

| Intermediate | Structure | Starting Materials | LCMS Data |
|---|---|---|---|
| 27 | (structure) | a) 5,7-Dichloro-2-trideuteromethyl-2H-pyrazolo [4,3-d] pyrimidine<br>b) Hexamethylditin | $R_t$ = 3.41 min, m/z [M + H]$^+$ = 334/336 (Method A) |

Intermediate 28 was prepared by an analogous reaction protocol as intermediate 22 using the appropriate starting materials (Table 5).

TABLE 5

| Intermediate | Structure | Starting Materials | LCMS Data |
|---|---|---|---|
| 28 | (structure) | a) Intermediate 20<br>b) Intermediate 27 | $R_t$ = 4.99 min, m/z [M + H]$^+$ = 537/539/541 (Method C) |

Intermediate 29 was prepared by an analogous reaction protocol as intermediate 23 using the appropriate starting material (Table 6).

TABLE 6

| Intermediate | Structure | Starting Materials | LCMS Data |
|---|---|---|---|
| 29 | (structure) | Intermediate 28 | $R_t$ = 3.77 min, m/z [M + H]$^+$ = 383/385/387 (Method B) |

Intermediates 30 and 31 were prepared by an analogous reaction protocol as intermediate 25 using the appropriate starting materials (Table 7).

TABLE 7

| Intermediate | Structure | Starting Materials | LCMS Data |
|---|---|---|---|
| 30 | 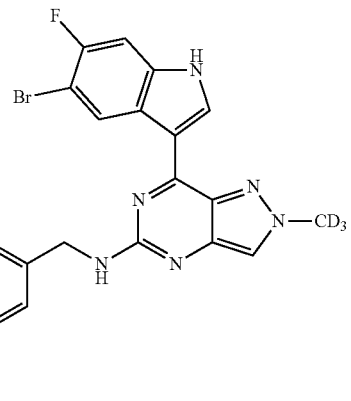 | a) Intermediate 29<br>b) 3,4,5-Trimethoxybenzylamine | $R_t$ = 2.69 min, m/z [M + H]$^+$ = 544/546 (Method C) |
| 31 | 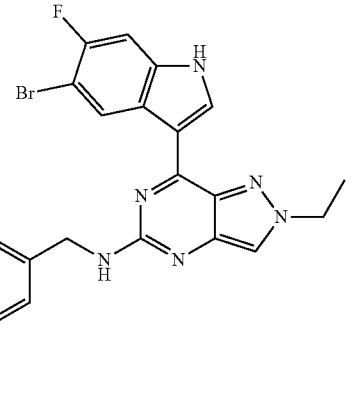 | a) Intermediate 23<br>b) 3,4,5-Trimethoxybenzylamine | $R_t$ = 2.76 min, m/z [M + H]$^+$ = 555/557 (Method C) |

Intermediates 32 and 33 were prepared by an analogous reaction protocol as intermediate 26 using the appropriate starting material (Table 8).

TABLE 8

| Intermediate | Structure | Starting Materials | LCMS Data |
|---|---|---|---|
| 32 | 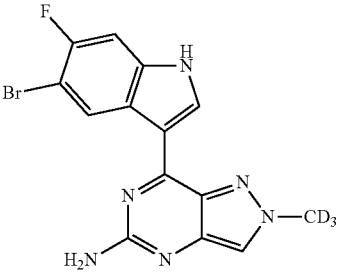 [SMILES: [2H]C([2H])([2H])n1cc2nc(N)nc(-c3c[nH]c4cc(F)c(Br)cc34)c2n1] | Intermediate 30 | $R_t$ = 2.08/2.28 min, m/z [M + H]$^+$ = 364/366 (Method B) |
| 33 | 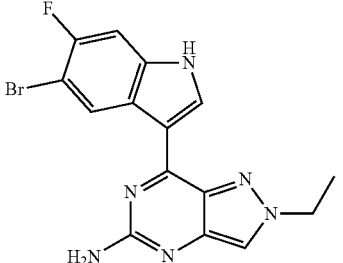 | Intermediate 31 | $R_t$ = 2.44 min, m/z [M + H]$^+$ = 375/377 (Method C) |

Example A6 a) Preparation of Intermediate 34

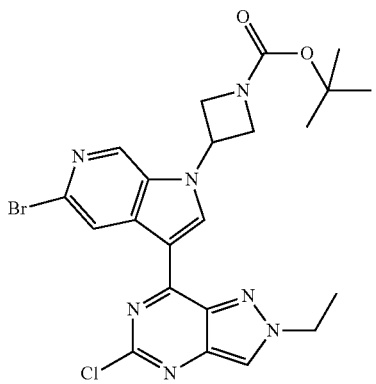 [SMILES: CCn1cc2nc(Cl)nc(-c3cn(C4CN(C(=O)OC(C)(C)C)C4)c4cnc(Br)cc34)c2n1]

A stirred mixture of intermediate 13 (1.70 g, 3.46 mmol), 3-iodo-azetidine-1-carboxylic acid tert-butyl ester (1.47 g, 5.18 mmol), $Cs_2CO_3$ (5.63 g, 17.3 mmol) and DMF (10 ml) was heated at 105° C. for 6.0 hours. A second portion of 3-iodo-azetidine-1-carboxylic acid tert-butyl ester (0.32 g, 1.14 mmol) and $Cs_2CO_3$ (2.25 g, 6.91 mmol) was added and the resulting mixture was heated at 105° C. for 18 hours. The mixture was cooled to ambient temperature and partitioned between water and DCM. The organic phase was dried over $Na_2SO_4$ and concentrated in vacuo. The residue was purified by column chromatography on silica gel, eluting with a mixture of MeOH and DCM (0:1 to 1:9 by volume), to afford the desired product (1.79 g, 100%).

LCMS (Method C): $R_t$=4.25 min, m/z [M+H]$^+$=532/534/536.

b) Preparation of Intermediate 35

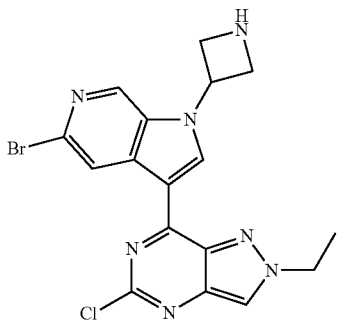 [SMILES: CCn1cc2nc(Cl)nc(-c3cn(C4CNC4)c4cnc(Br)cc34)c2n1]

A stirred solution of intermediate 34 (1.79 g, 3.36 mmol) in DCM (20 ml) under a nitrogen atmosphere at ambient temperature was treated with TFA (2.0 ml, 26.1 mmol), and the resulting mixture was stirred for 1 hour. The mixture was concentrated in vacuo to afford the desired product (1.84 g, 100%).

LCMS (Method C): $R_t$=2.27 min, m/z [M+H]$^+$=432/434/436.

c) Preparation of Intermediate 36

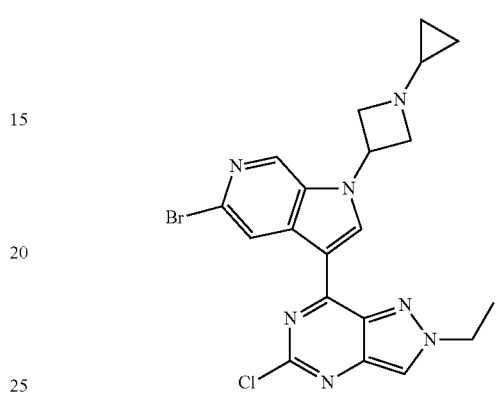

A stirred solution of intermediate 35 (1.84 g, 3.36 mmol) in a mixture of MeOH (17 ml) and acetic acid (8.0 ml) under nitrogen atmosphere at ambient temperature was treated with (1-ethoxycyclopropoxy)trimethylsilane (2.93 g, 16.8 mmol). After stirring for 10 minutes, the mixture was treated with sodium cyanoborohydride (1.60 g, 25.4 mmol) and the resulting mixture was stirred at 55° C. for 18 hours. The mixture was cooled to ambient temperature and concentrated in vacuo. The residue was partitioned between DCM and 2.0 M aqueous sodium carbonate solution. The organic phase was dried over $Na_2SO_4$ and concentrated in vacuo. The residue was purified by column chromatography on silica gel, eluting with a mixture of MeOH and DCM (0:1 to 1:9 by volume), to afford the desired product as a pale yellow solid (0.55 g, 35%).

LCMS (Method B): $R_t$=2.41 min, m/z [M+H]$^+$=472/474/476.

Intermediates 37 to 39 were prepared by an analogous reaction protocol as intermediate 34 using the appropriate starting materials (Table 9).

TABLE 9

| Intermediate | Structure | Starting Materials | LCMS Data |
|---|---|---|---|
| 37 | 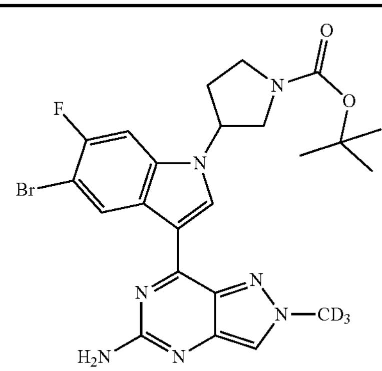 | a) Intermediate 32<br>b) 3-Methanesulfonyloxy-pyrrolidine-1-carboxylic acid tert-butyl ester | $R_t$ = 2.77 min,<br>m/z [M + H]$^+$ = 533/535<br>(Method C) |

TABLE 9-continued

| Intermediate | Structure | Starting Materials | LCMS Data |
|---|---|---|---|
| 38 | (structure) | a) Intermediate 33<br>b) 3-Methanesulfonyloxy-pyrrolidine-1-carboxylic acid tert-butyl ester | $R_t$ = 2.87 min, m/z [M + H]$^+$ = 544/546 (Method C) |
| 39 | (structure) | a) Intermediate 33<br>b) 3-Iodo-azetidine-1-carboxylic acid tert-butyl ester | $R_t$ = 2.93 min, m/z [M + H]$^+$ = 530/532 (Method C) |

Intermediates 40 to 42 were prepared by an analogous reaction protocol as intermediate 35 using the appropriate starting material (Table 10).

TABLE 10

| Intermediate | Structure | Starting Materials | LCMS Data |
|---|---|---|---|
| 40 | (structure) | Intermediate 37 | $R_t$ = 0.31/1.85 min, m/z [M + H]$^+$ = 433/435 (Method C) |

TABLE 10-continued

| Intermediate | Structure | Starting Materials | LCMS Data |
|---|---|---|---|
| 41 | 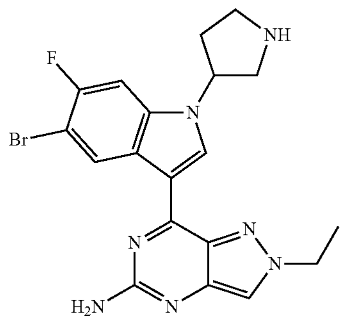 [SMILES: CCn1cc2nc(N)nc(-c3cn(C4CCNC4)c4cc(F)c(Br)cc34)c2n1] | Intermediate 38 | $R_t$ = 0.27/1.96 min, m/z [M + H]$^+$ = 444/446 (Method A) |
| 42 | 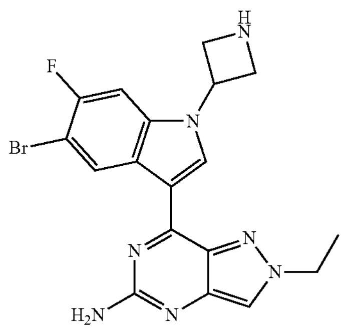 [SMILES: CCn1cc2nc(N)nc(-c3cn(C4CNC4)c4cc(F)c(Br)cc34)c2n1] | Intermediate 39 | $R_t$ = 0.33/1.88 min, m/z [M + H]$^+$ = 430/432 (Method C) |

Example A7 a) Preparation of Intermediate 43

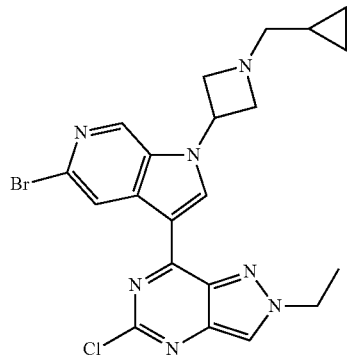 [SMILES: CCn1cc2nc(Cl)nc(-c3cn(C4CN(CC5CC5)C4)c4cnc(Br)cc34)c2n1]

A stirred solution of intermediate 35 (0.29 g, 0.67 mmol) in a mixture of MeOH (20 ml) and 1,2-dichloroethane (10 ml) under a nitrogen atmosphere at ambient temperature was treated sequentially with sodium acetate (0.06 g, 0.67 mmol), cyclopropanecarboxaldehyde (0.09 g, 0.67 mmol) and sodium triacetoxyborohydride (0.28 g, 1.34 mmol), and the resulting mixture was stirred for 4 hours. The mixture was purified by ISOLUTE® SCX-2 SPE column, eluting with a mixture of MeOH and 2.0 M ammonia solution in MeOH (1:0 to 0:1 by volume), to afford the desired product as a pale yellow solid (0.26 g, 79%).

LCMS (Method B): $R_t$=2.36 min, m/z [M+H]$^+$=486/488/490.

Intermediates 44 to 46 were prepared by an analogous reaction protocol as intermediate 43 using the appropriate starting materials (Table 11).

TABLE 11

| Intermediate | Structure | Starting Materials | LCMS Data |
|---|---|---|---|
| 44 | 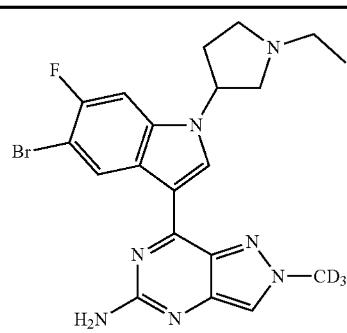 | a) Intermediate 40<br>b) Acetaldehyde | $R_t$ = 0.32/1.82 min, m/z [M + H]$^+$ = 461/463 (Method C) |

TABLE 11-continued

| Intermediate | Structure | Starting Materials | LCMS Data |
|---|---|---|---|
| 45 | 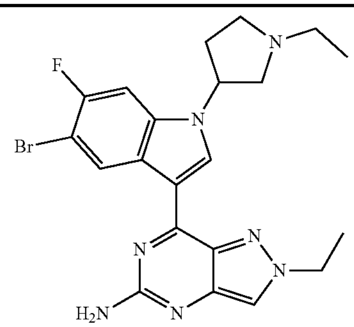 | a) Intermediate 41<br>b) Acetaldehyde | $R_t$ = 0.32/2.06 min, m/z [M + H]$^+$ = 472/474 (Method C) |
| 46 | 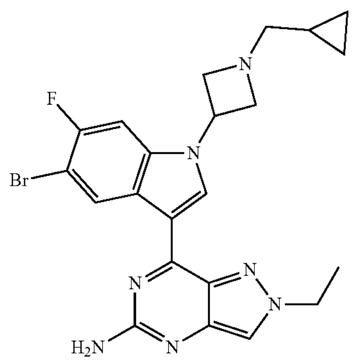 [SMILES: CCn1cc2nc(N)nc(-c3cn(C4CN(CC5CC5)C4)c4cc(F)c(Br)cc34)c2n1] | a) Intermediate 42<br>b) Cyclopropanecarboxaldehyde | $R_t$ = 1.80 min, m/z [M + H]$^+$ = 484/486 (Method B) |

Preparation of Compounds

The values of acid content (e.g. formic acid or acetic acid) in the compounds as provided herein, are those obtained experimentally and may vary when using different analytical methods. The content of formic acid or acetic acid reported herein was determined by $^1$H NMR integration and is reported together with the $^1$H NMR results.

Compounds with an acid content of below 0.5 equivalents may be considered as free bases.

Example B1 a) Preparation of Compound 1

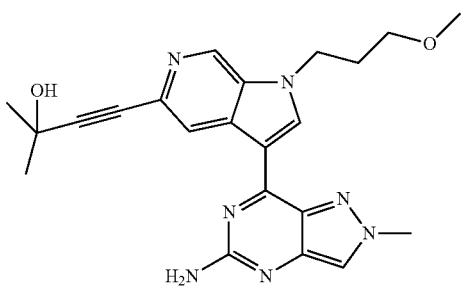 [SMILES: COCCCn1cc(-c2nc(N)nc3cn(C)nc23)c2cc(C#CC(C)(C)O)ncc21]

A stirred mixture of intermediate 8 (0.04 g, 0.10 mmol), 2-methyl-but-3-yn-2-ol (0.01 g, 0.13 mmol), tetrakis(triphenylphosphine) palladium (0.02 g, 0.02 mmol), copper(I) iodide (0.002 g, 0.011 mmol), Et$_3$N (0.10 ml, 0.74 mmol) and MeCN (1.0 ml) was heated by microwave irradiation at 100° C. for 1 hour. The mixture was cooled to ambient temperature and concentrated in vacuo. The residue was purified by column chromatography on silica gel eluting with a mixture of 2.0 M ammonia solution in MeOH and DCM (0:1 to 1:9 by volume). Further purification by trituration with Et$_2$O afforded the desired product as a pale yellow solid (0.02 g, 50%).

$^1$H NMR (400 MHz, DMSO-d$_6$) δ ppm: 8.95 (s, 1H), 8.93 (d, J=1.0 Hz, 1H), 8.74 (d, J=1.0 Hz, 1H), 8.00 (s, 1H), 6.26 (s, 2H), 5.48 (s, 1H), 4.51 (t, J=6.8 Hz, 2H), 4.16 (s, 3H), 3.29-3.26 (m, 2H), 3.24 (s, 3H), 2.12-2.03 (m, 2H), 1.52 (s, 6H).

LCMS (Method E): $R_t$=2.32 min, m/z [M+H]$^+$=420.

Compounds 2 to 4 were prepared by an analogous reaction protocol as Example B1 using the appropriate starting materials (Table 12).

TABLE 12

| Compound | Structure | Starting Materials |
|---|---|---|
| 2 | 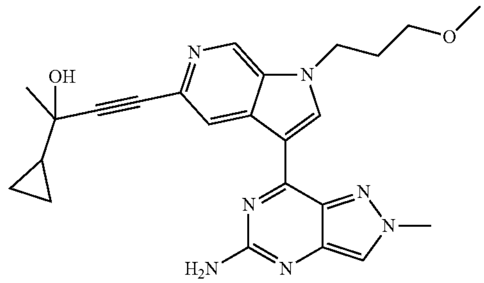 [SMILES: COCCCn1cc(-c2nc(N)nc3cn(C)nc23)c2cc(C#CC(C)(O)C3CC3)ncc21] | a) Intermediate 8<br>b) 2-Cyclopropyl-but-3-yn-2-ol |
| 3 | 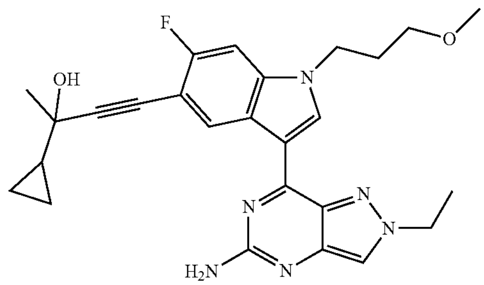 [SMILES: CCn1cc2nc(N)nc(-c3cn(CCCOC)c4cc(F)c(C#CC(C)(O)C5CC5)cc34)c2n1] | a) Intermediate 26<br>b) 2-Cyclopropyl-but-3-yn-2-ol |
| 4 | 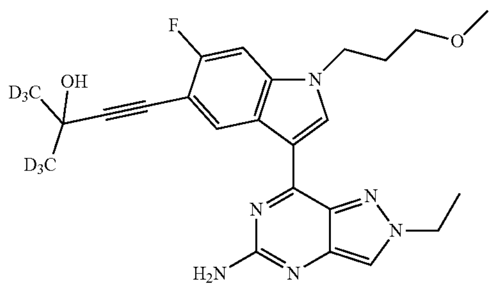 [SMILES: [2H]C([2H])([2H])C(O)(C#Cc1cc2c(-c3nc(N)nc4cn(CC)nc34)cn(CCCOC)c2cc1F)C([2H])([2H])[2H]] | a) Intermediate 26<br>b) 1,1,1-Trideutero-2-trideuteromethyl-3-butyn-2-ol |

Example B2 a) Preparation of Compound 5

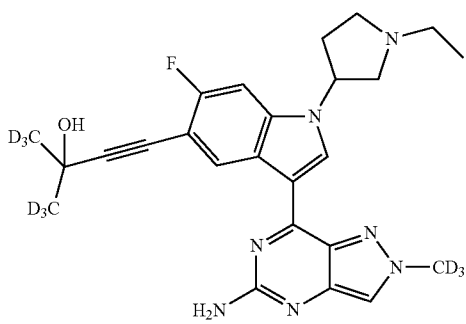 [SMILES: [2H]C([2H])([2H])n1cc2nc(N)nc(-c3cn(C4CCN(CC)C4)c4cc(F)c(C#CC(O)(C([2H])([2H])[2H])C([2H])([2H])[2H])cc34)c2n1]

A degassed mixture of intermediate 44 (0.07 g, 0.15 mmol), intermediate 1 (0.09 g, 0.30 mmol), tetrakis(triphenylphosphine) palladium (0.04 g, 0.03 mmol), copper(I) iodide (0.003 g, 0.02 mmol), Et$_3$N (0.15 ml, 1.06 mmol), MeCN (3.0 ml) and 1.0 M solution of TBAF in THF (0.08 ml, 0.08 mmol) was heated by microwave irradiation at 100° C. for 1 hour. The mixture cooled to ambient temperature and concentrated in vacuo. The residue was partitioned between EtOAc and water, and the organic phase was washed with brine, dried over Na$_2$SO$_4$ and concentrated in vacuo. The residue was purified by ISOLUTE® SCX-2 SPE column washing with MeOH, followed by elution with 2.0 M ammonia in MeOH. Further purification by reverse phase preparative HPLC, eluting with a mixture of MeCN and water containing 0.1% formic acid (1:9 to 3:1 by volume over 20 minutes), afforded the desired product as a pale yellow solid (0.02 g, 32%, contains formic acid 1.0 equivalents).

$^1$H NMR (400 MHz, DMSO-d$_6$) δ ppm: 9.20 (s, 1H), 8.84 (d, J=7.5 Hz, 1H), 8.17 (s, 1H), 7.97 (s, 1H), 7.77 (d, J=10.7 Hz, 1H), 6.17 (s, 2H), 5.43 (br. s, 1H), 5.22-5.15 (m, 1H), 3.19-3.09 (m, 2H), 2.68-2.52 (m, 4H), 2.34-2.25 (m, 1H), 1.92-1.81 (m, 1H), 1.18 (t, J=7.2 Hz, 3H).

LCMS (Method E): R$_t$=2.11 min, m/z [M+H]$^+$=471.

Compounds 6 and 7 were prepared by an analogous reaction protocol as Example B2 using the appropriate starting materials (Table 13).

TABLE 13

| Compound | Structure | Starting Materials |
|---|---|---|
| 6 | 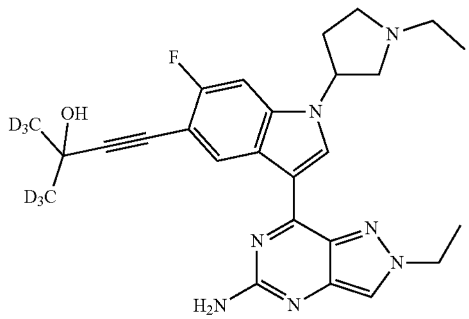 [SMILES: [2H]C([2H])([2H])C(O)(C#Cc1cc2c(-c3nc(N)nc4cn(CC)nc34)cn(C3CCN(CC)C3)c2cc1F)C([2H])([2H])[2H]] | a) Intermediate 45<br>b) Intermediate 1 |
| 7 | 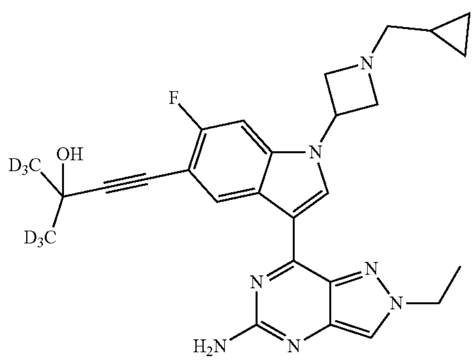 [SMILES: [2H]C([2H])([2H])C(O)(C#Cc1cc2c(-c3nc(N)nc4cn(CC)nc34)cn(C3CN(CC4CC4)C3)c2cc1F)C([2H])([2H])[2H]] | a) Intermediate 46<br>b) Intermediate 1 |

Example B3 a) Preparation of Compound 8

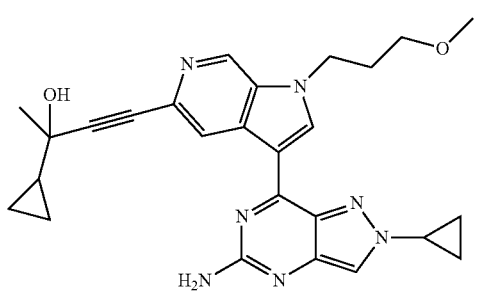 [SMILES: COCCCn1cc(-c2nc(N)nc3cn(C4CC4)nc23)c2cc(C#CC(C)(O)C3CC3)ncc21]

A degassed mixture of intermediate 12 (0.21 g, 0.43 mmol), acetamide (0.03 g, 0.54 mmol), potassium carbonate (0.18 g, 1.28 mmol), palladium (II) acetate (0.01 g, 0.08 mmol), Xantphos (0.05 g, 0.09 mmol) and 1,4-dioxane (4.0 ml) under an Argon atmosphere was heated by microwave irradiation at 110° C. for 30 minutes. The mixture was cooled to ambient temperature, filtered through Celite® and the filtrate concentrated in vacuo. The residue was diluted with MeOH (8.0 ml), treated with 1.0 M aqueous sodium hydroxide solution (4.0 ml), and the resulting mixture heated at reflux for 30 minutes. The mixture was cooled to ambient temperature and partitioned between chloroform and water. The organic phase was dried over $Na_2SO_4$ and concentrated in vacuo. The residue was purified by reverse phase preparative HPLC, eluting with a mixture of MeCN and water containing 0.1% ammonium hydroxide (1:9 to 19:1 by volume over 20 minutes), to afford the desired product as a pale yellow solid (0.08 g, 39%).

$^1$H NMR (400 MHz, DMSO-d$_6$) δ ppm: 8.93 (d, J=1.0 Hz, 1H), 8.91 (s, 1H), 8.72 (d, J=1.0 Hz, 1H), 8.11 (s, 1H), 6.24 (s, 2H), 5.33 (s, 1H), 4.51 (t, J=6.7 Hz, 2H), 4.15-4.08 (m, 1H), 3.27 (t, J=6.0 Hz, 2H), 3.24 (s, 3H), 2.12-2.02 (m, 2H), 1.54 (s, 3H), 1.38-1.32 (m, 2H), 1.20-1.11 (m, 3H), 0.60-0.50 (m, 2H), 0.47-0.36 (m, 2H).

LCMS (Method E): R$_t$=2.84 min, m/z [M+H]$^+$=472.

Compounds 9 to 12 were prepared by an analogous reaction protocol as Example B3 using the appropriate starting materials (Table 14).

TABLE 14

| Compound | Structure | Starting Materials |
|---|---|---|
| 9 | 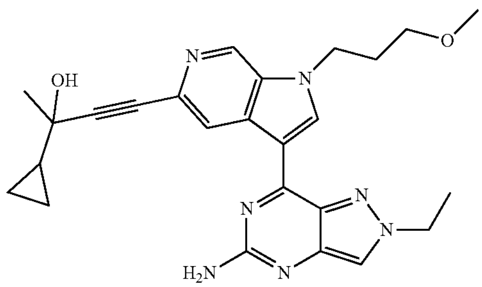 [SMILES: CCn1cc2nc(N)nc(-c3cn(CCCOC)c4cnc(C#CC(C)(O)C5CC5)cc34)c2n1] | a) Intermediate 15<br>b) Acetamide |
| 10 | 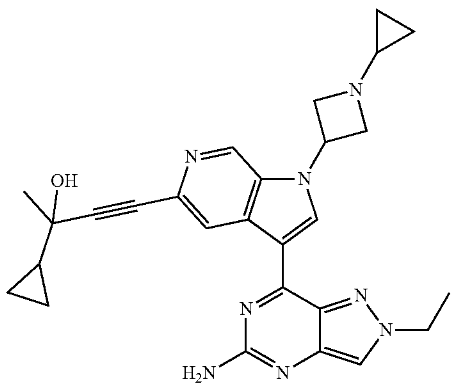 [SMILES: CCn1cc2nc(N)nc(-c3cn(C4CN(C5CC5)C4)c4cnc(C#CC(C)(O)C5CC5)cc34)c2n1] | a) Intermediate 16<br>b) Acetamide |
| 11 | 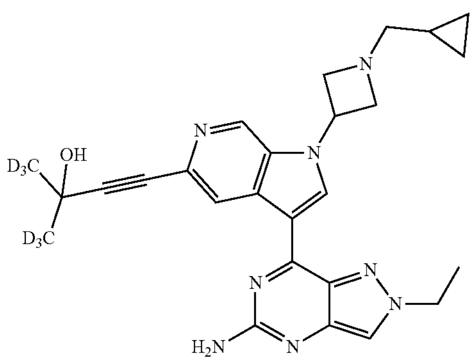 [SMILES: [2H]C([2H])([2H])C(O)(C#Cc1cc2c(-c3nc(N)nc4cn(CC)nc34)cn(C3CN(CC4CC4)C3)c2cn1)C([2H])([2H])[2H]] | a) Intermediate 17<br>b) Acetamide |
| 12 | 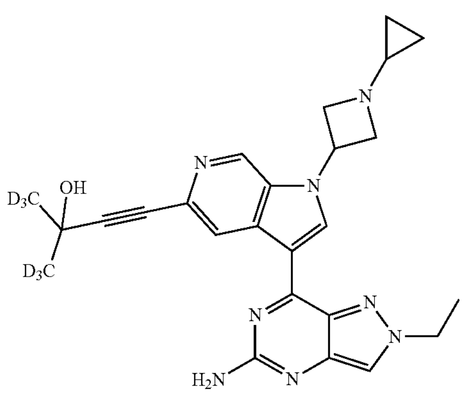 [SMILES: [2H]C([2H])([2H])C(O)(C#Cc1cc2c(-c3nc(N)nc4cn(CC)nc34)cn(C3CN(C4CC4)C3)c2cn1)C([2H])([2H])[2H]] | a) Intermediate 18<br>b) Acetamide |

Analytical Part

LCMS

Mass Spectrometry (LCMS) experiments to determine retention times and associated mass ions were performed using the following methods:

Method A: Experiments were performed on a Waters ZMD quadrupole mass spectrometer linked to a Waters 1525 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% MeCN containing 0.1% formic acid (solvent B) for the first 0.5 minute followed by a gradient up to 5% solvent A and 95% solvent B over the next 4 min. The final solvent system was held constant for a further 1 minute.

Method B: Experiments were performed on a Waters VG Platform II quadrupole spectrometer linked to a Hewlett Packard 1050 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% MeCN containing 0.1% formic acid (solvent B) for the first 0.3 minute followed by a gradient up to 5% solvent A and 95% solvent B over the next 4 min. The final solvent system was held constant for a further 1 minute.

Method C: Experiments were performed on a Waters Platform LC quadrupole mass spectrometer linked to a Hewlett Packard HP1100 LC system with diode array detector. The spectrometer had an electrospray source operating in positive and negative ion mode. Additional detection was achieved using a Sedex 85 evaporative light scattering detector. LC was carried out using a Phenomenex Luna 3micron 30×4.6 mm C18 column and a 2 mL/minute flow rate. The initial solvent system was 95% water containing 0.1% formic acid (solvent A) and 5% MeCN containing 0.1% formic acid (solvent B) for the first 0.5 minute followed by a gradient up to 5% solvent A and 95% solvent B over the next 4 min. The final solvent system was held constant for a further 1 minute.

Method D: Experiments were performed on a Waters ZQ quadrupole mass spectrometer linked to a Hewlett Packard HP1100 LC system with quaternary pump and PDA detector. The spectrometer had an electrospray source operating in positive and negative ion mode. Additional detection was achieved using a Sedex 65 evaporative light scattering detector. LC was carried out using a Phenomenex Luna 3 micron 30×4.6 mm C18 column and a 2 mL/minute flow rate. The initial solvent system was 95% water containing 0.1% formic acid (solvent A) and 5% MeCN containing 0.1% formic acid (solvent B) for the first 0.3 minute followed by a gradient up to 5% solvent A and 95% solvent B over the next 4 min. The final solvent system was held constant for a further 1 minute.

Method E: Experiments were performed on a Waters Micromass ZQ2000 quadrupole mass spectrometer linked to a Waters Acquity UPLC system with a PDA UV detector. The spectrometer had an electrospray source operating in positive and negative ion mode. LC was carried out using an Acquity BEH 1.7micron C18 column, an Acquity BEH Shield 1.7micron RP18 column or an Acquity HST 1.8micron column. Each column has dimensions of 100×2.1 mm and was maintained at 40° C. with a flow rate of 0.4 mL/minute. The initial solvent system was 95% water containing 0.1% formic acid (solvent A) and 5% MeCN containing 0.1% formic acid (solvent B) for the first 0.4 minute followed by a gradient up to 5% solvent A and 95% solvent B over the next 5.2 min. The final solvent system was held constant for a further 0.8 min.

NMR Data

The NMR experiments herein were carried out using a Varian Unity Inova spectrometer with standard pulse sequences, operating at 400 MHz at ambient temperature. Chemical shifts ($\delta$) are reported in parts per million (ppm) downfield from tetramethylsilane (TMS), which was used as internal standard. DMSO-$d_6$ (deuterated DMSO, dimethyl-d6 sulfoxide) was used as solvent.

The values of acid content (e.g. formic acid or acetic acid) in the compounds as provided herein, are those obtained experimentally and may vary when using different analytical methods. The content of formic acid or acetic acid reported herein was determined by $^1$H NMR integration. Compounds with an acid content of below 0.5 equivalents may be considered as free bases.

Compound 2
$^1$H NMR (400 MHz, DMSO-$d_6$) $\delta$ ppm: 8.95 (s, 1H), 8.92 (d, J=0.9 Hz, 1H), 8.72 (d, J=1.0 Hz, 1H), 8.00 (s, 1H), 6.23 (s, 2H), 5.33 (br. s, 1H), 4.50 (t, J=6.8 Hz, 2H), 4.15 (s, 3H), 3.28 (t, J=6.1 Hz, 2H), 3.24 (s, 3H), 2.11-2.02 (m, 2H), 1.54 (s, 3H), 1.21-1.13 (m, 1H), 0.62-0.48 (m, 2H), 0.47-0.36 (m, 2H).
LCMS (Method E): $R_t$=2.52 min, m/z [M+H]$^+$=446.

Compound 3 (Formic Acid 0.7 Equivalents)
$^1$H NMR (400 MHz, DMSO-$d_6$) $\delta$ ppm: 8.85 (s, 1H), 8.83 (d, J=7.5 Hz, 1H), 8.19 (s, 0.7H), 8.03 (s, 1H), 7.58 (d, J=10.4 Hz, 1H), 6.16 (s, 2H), 5.33 (br. s, 1H), 4.42 (q, J=7.3 Hz, 2H), 4.35 (t, J=6.9 Hz, 2H), 3.28-3.25 (m, 5H), 2.05-1.96 (m, 2H), 1.55 (s, 3H), 1.52 (t, J=7.3 Hz, 3H), 1.19-1.12 (m, 1H), 0.64-0.58 (m, 1H), 0.53-0.46 (m, 1H), 0.46-0.36 (m, 2H).
LCMS (Method E): $R_t$=3.73 min, m/z [M+H]$^+$=477.
A second batch was isolated with 0.6 equivalents of formic acid present.

Compound 4 (Formic Acid 1.0 Equivalents)
$^1$H NMR (400 MHz, DMSO-$d_6$) $\delta$ ppm: 8.85 (t, J=3.7 Hz, 2H), 8.13 (s, 1H), 8.03 (s, 1H), 7.58 (d, J=10.4 Hz, 1H), 6.19 (s, 2H), 5.42 (br. s, 1H), 4.42 (q, J=7.3 Hz, 2H), 4.35 (t, J=6.8 Hz, 2H), 3.28-3.25 (m, 5H), 2.05-1.96 (m, 2H), 1.52 (t, J=7.3 Hz, 3H).
LCMS (Method E): $R_t$=3.45 min, m/z [M+H]$^+$=457.

Compound 6
$^1$H NMR (400 MHz, DMSO-$d_6$) $\delta$ ppm: 9.22 (s, 1H), 8.84 (d, J=7.6 Hz, 1H), 8.02 (s, 1H), 7.76 (d, J=10.8 Hz, 1H), 6.17 (s, 2H), 5.42 (s, 1H), 5.22-5.15 (m, 1H), 4.40 (q, J=7.3 Hz, 2H), 3.21-3.09 (m, 2H), 2.67-2.51 (m, 4H), 2.32-2.24 (m, 1H), 1.91-1.81 (m, 1H), 1.54 (t, J=7.3 Hz, 3H), 1.17 (t, J=7.2 Hz, 3H).
LCMS (Method E): $R_t$=2.22 min, m/z [M+H]$^+$=482.

Compound 7
$^1$H NMR (400 MHz, DMSO-$d_6$) $\delta$ ppm: 9.22 (s, 1H), 8.86 (d, J=7.5 Hz, 1H), 8.05 (s, 1H), 7.69 (d, J=10.5 Hz, 1H), 6.22 (s, 2H), 5.44 (s, 1H), 5.27-5.19 (m, 1H), 4.43 (q, J=7.3 Hz, 2H), 3.85 (t, J=7.6 Hz, 2H), 3.45-3.40 (m, 2H), 2.43 (d, J=6.6 Hz, 2H), 1.56 (t, J=7.3 Hz, 3H), 0.87-0.79 (m, 1H), 0.47-0.41 (m, 2H), 0.18-0.13 (m, 2H).
LCMS (Method E): $R_t$=2.30 min, m/z [M+H]$^+$=494.

Compound 9
$^1$H NMR (400 MHz, DMSO-$d_6$) $\delta$ ppm: 8.95 (s, 1H), 8.93 (d, J=1.0 Hz, 1H), 8.73 (d, J=1.0 Hz, 1H), 8.06 (s, 1H), 6.23 (s, 2H), 5.33 (s, 1H), 4.51 (t, J=6.5 Hz, 2H), 4.44 (q, J=7.3 Hz, 2H), 3.28-3.25 (m, 2H), 3.24 (s, 3H), 2.11-2.03 (m, 2H), 1.56-1.51 (m, 6H), 1.21-1.13 (m, 1H), 0.62-0.49 (m, 2H), 0.47-0.35 (m, 2H).
LCMS (Method E): $R_t$=2.77 min, m/z [M+H]$^+$=460.

Compound 10
$^1$H NMR (400 MHz, DMSO-$d_6$) $\delta$ ppm: 9.29 (s, 1H), 9.00 (d, J=1.0 Hz, 1H), 8.74 (d, J=1.0 Hz, 1H), 8.07 (s, 1H), 6.26 (s, 2H), 5.39-5.32 (m, 2H), 4.44 (q, J=7.3 Hz, 2H), 3.93 (t, J=7.6 Hz, 2H), 3.61-3.55 (m, 2H), 2.12-2.05 (m, 1H), 1.59-1.54 (m, 6H), 1.22-1.14 (m, 1H), 0.63-0.49 (m, 2H), 0.48-0.37 (m, 4H), 0.36-0.31 (m, 2H).

LCMS (Method E): $R_t$=2.17 min, m/z $[M+H]^+$=483.

Compound 11

$^1$H NMR (400 MHz, DMSO-$d_6$) δ ppm: 9.31 (s, 1H), 9.03 (d, J=1.0 Hz, 1H), 8.76 (d, J=1.0 Hz, 1H), 8.07 (s, 1H), 6.28 (s, 2H), 5.47 (s, 1H), 5.44-5.36 (m, 1H), 4.45 (q, J=7.3 Hz, 2H), 3.87 (t, J=7.6 Hz, 2H), 3.52-3.47 (m, 2H), 2.44 (d, J=6.7 Hz, 2H), 1.56 (t, J=7.3 Hz, 3H), 0.88-0.79 (m, 1H), 0.47-0.41 (m, 2H), 0.19-0.14 (m, 2H).

LCMS (Method E): $R_t$=1.96 min, m/z $[M+H]^+$=477.

Compound 12 (Formic Acid 1.0 Equivalents)

$^1$H NMR (400 MHz, DMSO-$d_6$) δ ppm: 9.30 (s, 1H), 9.00 (d, J=1.0 Hz, 1H), 8.75 (d, J=1.1 Hz, 1H), 8.29 (s, 1H), 8.07 (s, 1H), 6.28 (s, 2H), 5.46 (br. s, 1H), 5.40-5.33 (m, 1H), 4.44 (q, J=7.3 Hz, 2H), 3.93 (t, J=7.6 Hz, 2H), 3.61-3.55 (m, 2H), 2.11-2.05 (m, 1H), 1.56 (t, J=7.3 Hz, 3H), 0.47-0.41 (m, 2H), 0.37-0.33 (m, 2H).

LCMS (Method E): $R_t$=1.96 min, m/z $[M+H]^+$=463.

Pharmacological Part

Biological Assay A

Inhibition of Auto-Phosphorylation of Recombinant Human NF-kappaB-Inducing Kinase (NIK/MAP3K14) Activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and $IC_{50}$'s were determined by fitting a sigmoidal curve to % inhibition of control versus $Log_{10}$ compound concentration.

Biological Assay B

Effect of Compounds on P-IKKα Levels in L363 Cells

All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of 0.2×$10^6$ cells per ml—1×$10^6$ cells per ml at 37° C. in a humidified 5% $CO_2$ atmosphere. Cells were passaged twice a week splitting back to obtain the low density. Cells were seeded in 96 well plates (Nunc 167008) at 2×$10^6$ per ml media in a volume of 75 μl per well plus 25 μl 1 μg/ml recombinant human B-cell activating factor (BAFF/BLyS/TNFSF13B). Seeded cells were incubated at 37° C. in a humidified 5% $CO_2$ atmosphere for 24 hr. Drugs and/or solvents were added (20 μl) to a final volume of 120 μl. Following 2 hr treatment plates were removed from the incubator and cell lysis was achieved by the addition of 30 μl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 μM ADS125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Biological Assay C

Determination of Antiproliferative Activity on LP-1, L-363 and JJN-3 Cells

All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human LP-1, L-363 and JJN-3 cells (DSMZ) were cultured in RPMI 1640 medium supplemented with 2 mM L-glutamine, and 10% fetal calf serum (PAA). Cells were routinely kept as suspension cells at 37° C. in a humidified 5% $CO_2$ atmosphere. Cells were passaged at a seeding density of 0.2×$10^6$/ml twice a week. Cells were seeded in black tissue culture treated 96-well plates (Perkin Elmer). Densities used for plating ranged from 2,000 to 6,000 cells per well in a total volume of 75 μl medium. After twenty four hours, drugs and/or solvents were added (25 μl) to a final volume of 100 μl. Following 72 hr of treatment plates were removed from the incubator and allowed to equilibrate to room temperature for approx 10 min. 100 μl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table 15 (the values in Table 15 are averaged values over all measurements on all batches of a compound).

TABLE 15

| Compound | AlphaScreen IC50 (nM) | IKKα Cellular $IC_{50}$ (nM) | JJN-3 $EC_{50}$ (nM) | L-363 $EC_{50}$ (nM) | LP-1 $EC_{50}$ (nM) |
|---|---|---|---|---|---|
| 1 | 46 | n.c. | 538 | 655 | 6783 |
| 2 | 23 | 103 | 358 | 386 | 2957 |
| 3 | 992 | n.c. | 182 | 246 | 845 |
| 4 | 65 | n.c. | 102 | 69 | 244 |
| 5 | 112 | n.c. | 46 | 52 | 128 |
| 6 | 37 | n.c. | 40 | 38 | 70 |
| 7 | 60 | n.c. | 95 | 53 | 202 |
| 8 | 38 | n.c. | 78 | 76 | 402 |
| 9 | 52 | n.c. | 217 | 162 | 629 |
| 10 | 186 | n.c. | 406 | 241 | 788 |

TABLE 15-continued

| Compound | Alpha-Screen IC50 (nM) | IKKα Cellular IC$_{50}$ (nM) | JJN-3 EC$_{50}$ (nM) | L-363 EC$_{50}$ (nM) | LP-1 EC$_{50}$ (nM) |
|---|---|---|---|---|---|
| 11 | 143 | n.c. | 158 | 62 | 1178 |
| 12 | 84 | n.c. | 301 | 140 | 877 | n.c.: not calculated

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Waler | ad 100 g |

In this Example, active ingredient can be replaced with the same amount of any of the compounds according to the present invention, in particular by the same amount of any of the exemplified compounds.

The invention claimed is:

1. A method of treating cancer in a warm-blooded animal which comprises administering to the said animal an effective amount of a compound of Formula (I):

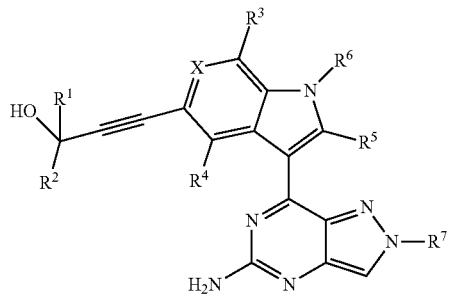

or a tautomer or a stereoisomeric form thereof, wherein
$R^1$ is selected from the group of hydrogen; $C_{1-4}$alkyl; and $C_{1-4}$alkyl substituted with one or more fluoro substituents;
$R^2$ is selected from the group of hydrogen; $C_{1-4}$alkyl; $C_{1-4}$alkyl substituted with one or more fluoro substituents; $C_{3-6}$cycloalkyl; and Het$^1$;
or $R^1$ and $R^2$ together with the carbon atom to which they are attached form a $C_{3-6}$cycloalkyl;
Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, $C_{1-4}$alkyl, $C_{1-4}$alkyloxy, $C_{1-4}$alkyl substituted with one or more fluoro substituents, and $C_{1-4}$alkyloxy substituted with one or more fluoro substituents;
X is N or CR$^9$;
$R^9$ is selected from hydrogen and halogen;
$R^3$ is selected from the group of hydrogen; halogen; cyano; $C_{3-6}$cycloalkyl; $C_{1-6}$alkyl; Het$^4$; $C_{1-6}$alkyl substituted with one or more fluoro substituents; —OC$_{1-6}$alkyl;
—OC$_{1-6}$alkyl substituted with one or more fluoro substituents; and $C_{1-6}$alkyl substituted with one substituent selected from —NR$^{3a}$R$^{3b}$ and —OC$_{1-4}$alkyl;
Het$^4$ is a heteroaryl selected from the group of piperidinyl, tetrahydropyranyl, pyrrolidinyl, tetrahydrofuranyl, azetidinyl, piperazinyl, morpholinyl and oxetanyl, each of which may be optionally substituted with one or two substituents independently selected from fluoro, $C_{1-4}$alkyl, —OC$_{1-4}$alkyl, $C_{3-6}$cycloalkyl and $C_{1-4}$alkyl substituted with one or more fluoro substituents;
$R^{3a}$ and $R^{3b}$ are each independently selected from hydrogen and $C_{1-4}$alkyl;
$R^4$ is hydrogen;
$R^5$ is selected from the group of hydrogen; cyano; $C_{1-4}$alkyl; $C_{1-4}$alkyl substituted with one or more fluoro substituents; $C_{1-4}$alkyl substituted with one substituent selected from the group of —NR$^{5a}$R$^{5b}$, —OC$_{1-4}$alkyl, and Het$^5$;
$R^{5a}$ and $R^{5b}$ are each independently selected from the group of hydrogen and $C_{1-4}$alkyl;
Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —OC$_{1-4}$alkyl, $C_{3-6}$cycloalkyl and $C_{1-4}$alkyl substituted with one or more fluoro substituents;
$R^6$ is selected from the group of hydrogen; Het$^2$; $R^8$; $C_{1-6}$alkyl optionally substituted with one Het$^3$; and $C_{2-6}$alkyl substituted with one or more substituents independently selected from the group of fluoro, NR$^{6a}$R$^{6b}$, and —OR$^{6c}$;
$R^{6a}$ and $R^{6b}$ and $R^{6c}$ are each independently selected from hydrogen and $C_{1-6}$alkyl;
Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —OC$_{1-4}$alkyl, $C_{3-6}$cycloalkyl, $C_{1-4}$alkyl substituted with one —OC$_{1-4}$alkyl, $C_{1-4}$alkyl substituted with one $C_{3-6}$cycloalkyl, and C$_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, C$_{1-4}$alkyl, —OC$_{1-4}$alkyl, C$_{3-6}$cycloalkyl, C$_{1-4}$alkyl substituted with one —OC$_{1-4}$alkyl, C$_{1-4}$alkyl substituted with one C$_{3-6}$cycloalkyl, and C$_{1-4}$alkyl substituted with one or more fluoro substituents;

R$^8$ is C$_{3-6}$cycloalkyl optionally substituted with one or two substituents independently selected from fluoro, C$_{1-4}$alkyl, —OC$_{1-4}$alkyl, C$_{1-4}$alkyl substituted with one —OC$_{1-4}$alkyl, and C$_{1-4}$alkyl substituted with one or more fluoro substituents;

R$^7$ is selected from the group of hydrogen, C$_{1-6}$alkyl, C$_{3-6}$cycloalkyl and C$_{1-4}$alkyl substituted with one —OC$_{1-4}$alkyl;

or a pharmaceutically acceptable addition salt, or a solvate thereof.

2. The method according to claim 1, wherein

R$^1$ is selected from the group of hydrogen; C$_{1-4}$alkyl; and C$_{1-4}$alkyl substituted with one or more fluoro substituents;

R$^2$ is selected from the group of C$_{1-4}$alkyl; C$_{1-4}$alkyl substituted with one or more fluoro substituents; C$_{3-6}$cycloalkyl; and Het$^1$;

or R$^1$ and R$^2$ together with the carbon atom to which they are attached form a C$_{3-6}$cycloalkyl;

Het$^1$ is a heteroaryl selected from the group of thienyl, thiazolyl, pyrrolyl, oxazolyl, oxadiazolyl, pyrazolyl, imidazolyl, isoxazolyl, isothiazolyl, pyridinyl and pyrimidinyl, each of which may be optionally substituted with one or two substituents independently selected from halogen, cyano, C$_{1-4}$alkyl, C$_{1-4}$alkyloxy, C$_{1-4}$alkyl substituted with one or more fluoro substituents, and C$_{1-4}$alkyloxy substituted with one or more fluoro substituents;

X is N or CR$^9$;

R$^9$ is selected from hydrogen and halogen;

R$^3$ is selected from the group of hydrogen; halogen; cyano; C$_{3-6}$cycloalkyl; C$_{1-6}$alkyl; C$_{1-6}$alkyl substituted with one or more fluoro substituents; —OC$_{1-6}$alkyl; —OC$_{1-6}$alkyl substituted with one or more fluoro substituents; and C$_{1-6}$alkyl substituted with one substituent selected from —NR$^{3a}$R$^{3b}$ and —OC$_{1-4}$alkyl;

R$^{3a}$ and R$^{3b}$ are each independently selected from hydrogen and C$_{1-4}$alkyl;

R$^4$ is hydrogen;

R$^5$ is selected from the group of hydrogen; cyano; C$_{1-4}$alkyl; C$_{1-4}$alkyl substituted with one or more fluoro substituents; C$_{1-4}$alkyl substituted with one substituent selected from the group of —NR$^{5a}$R$^{5b}$, and —OC$_{1-4}$alkyl;

R$^{5a}$ and R$^{5b}$ are each independently selected from the group of hydrogen and C$_{1-4}$alkyl;

R$^6$ is selected from the group of hydrogen; Het$^2$; R$^8$; C$_{1-6}$alkyl optionally substituted with one Het$^3$; and C$_{2-6}$alkyl substituted with one or more substituents independently selected from the group of fluoro, —NR$^{6a}$R$^{6b}$, and —OR$^{6c}$;

R$^{6a}$, R$^{6b}$ and R$^{6c}$ are each independently selected from hydrogen and C$_{1-6}$alkyl;

Het$^2$ is a heterocyclyl, bound through any available carbon atom, selected from the group of piperidinyl, tetrahydropyranyl, pyrrolidinyl, tetrahydrofuranyl, azetidinyl and oxetanyl, each of which may be optionally substituted with one or two substituents independently selected from fluoro, C$_{1-4}$alkyl, —OC$_{1-4}$alkyl, C$_{3-6}$cycloalkyl, C$_{1-4}$alkyl substituted with one —OC$_{1-4}$alkyl, C$_{1-4}$alkyl substituted with one C$_{3-6}$cycloalkyl, and C$_{1-4}$alkyl substituted with one or more fluoro substituents;

Het$^3$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, C$_{1-4}$alkyl, —OC$_{1-4}$alkyl, C$_{3-6}$cycloalkyl, C$_{1-4}$alkyl substituted with one —OC$_{1-4}$alkyl, C$_{1-4}$alkyl substituted with one C$_{3-6}$cycloalkyl, and C$_{1-4}$alkyl substituted with one or more fluoro substituents;

R$^8$ is C$_{3-6}$cycloalkyl optionally substituted with one or two substituents independently selected from fluoro, C$_{1-4}$alkyl, —OC$_{1-4}$alkyl, C$_{1-4}$alkyl substituted with one —OC$_{1-4}$alkyl, and C$_{1-4}$alkyl substituted with one or more fluoro substituents;

R$^7$ is selected from the group of hydrogen, C$_{1-6}$alkyl, C$_{3-6}$cycloalkyl and C$_{1-4}$alkyl substituted with one —OC$_{1-4}$alkyl.

3. The method according to claim 1, wherein

R$^1$ is C$_{1-4}$alkyl;

R$^2$ is selected from the group of C$_{1-4}$alkyl; and C$_{3-6}$cycloalkyl;

X is N or CR$^9$;

R$^9$ is halogen; in particular fluoro;

R$^3$ is hydrogen;

R$^4$ is hydrogen;

R$^5$ is hydrogen;

R$^6$ is selected from the group of Het$^2$; and C$_{2-6}$alkyl substituted with one —OR$^{6c}$;

R$^{6c}$ is C$_{1-6}$alkyl;

Het$^2$ is a heterocyclyl, bound through any available carbon atom, selected from the group of pyrrolidinyl, and oxetanyl, each of which may be optionally substituted with one or two substituents independently selected from C$_{1-4}$alkyl, C$_{3-6}$cycloalkyl, and C$_{1-4}$alkyl substituted with one C$_{3-6}$cycloalkyl;

R$^7$ is selected from the group of C$_{1-6}$alkyl, and C$_{3-6}$cycloalkyl.

4. The method according to claim 1, wherein

R$^3$ is hydrogen; and R$^5$ is hydrogen.

5. The method according to claim 1,

R$^6$ is selected from the group of Het$^2$; and C$_{2-6}$alkyl substituted with one —OR$^{6c}$.

6. The method according to claim 5, wherein R$^6$ is selected from the group of

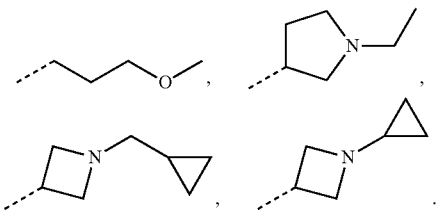

7. The method according to claims 1 to 6, $R^1$ is selected from the group of $C_{1-4}$alkyl;

$R^2$ is selected from the group of $C_{1-4}$alkyl; $C_{1-4}$alkyl substituted with one or more fluoro substituents; $C_{3-6}$cycloalkyl; and $Het^1$;

or $R^1$ and $R^2$ together with the carbon atom to which they are attached form a $C_{3-6}$cycloalkyl.

8. The method according to claims 1 to 6, wherein X is N.

9. The method according to claims 1 to 6, wherein X is $CR^9$.

10. The method according to claim 1, wherein the compound is selected from

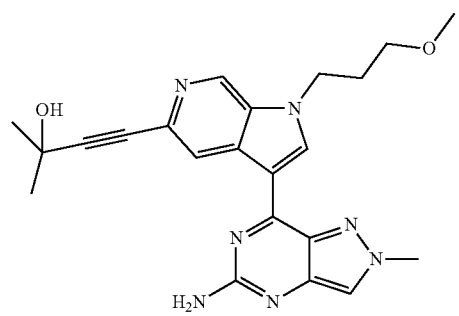

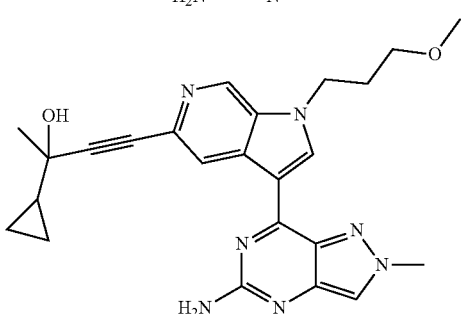

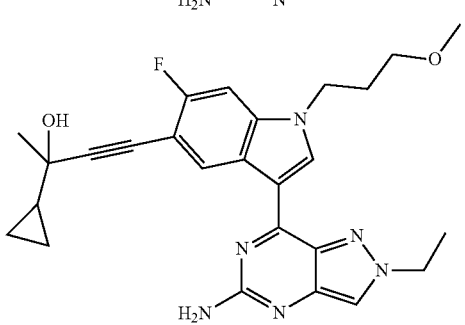

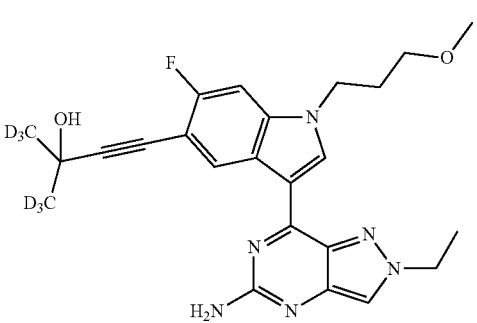

-continued

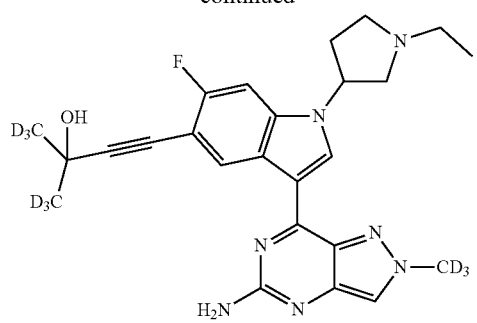

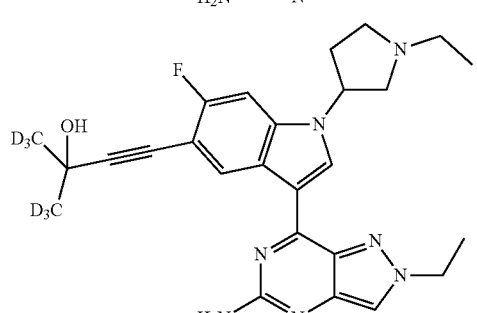

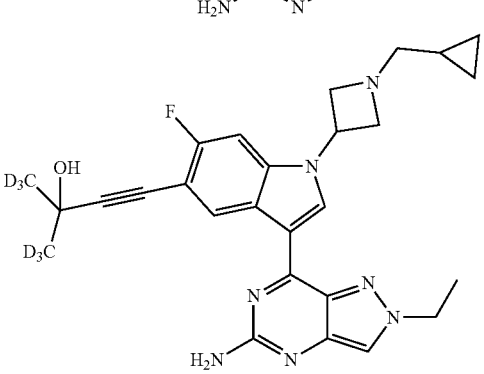

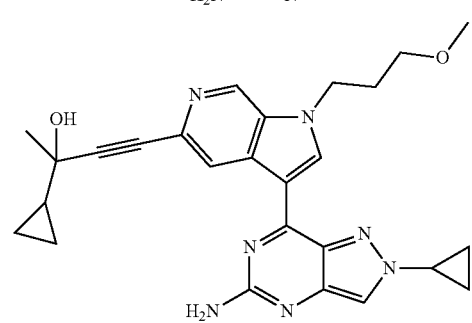

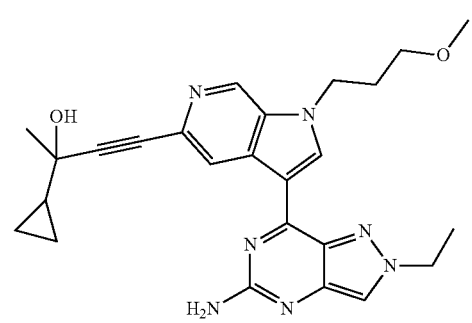

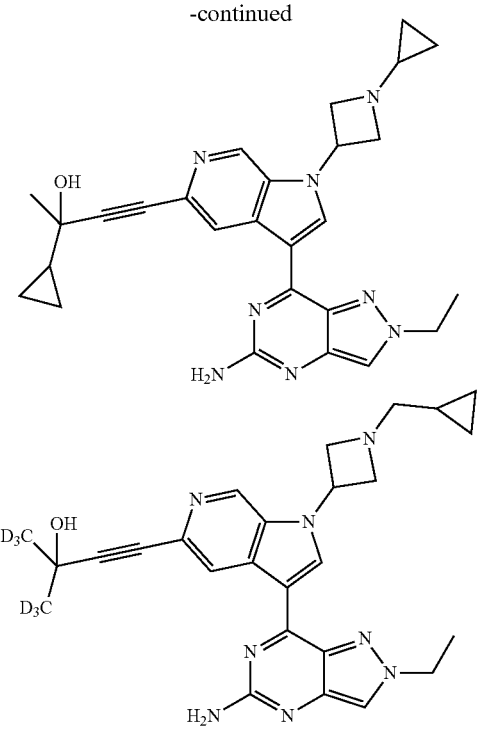

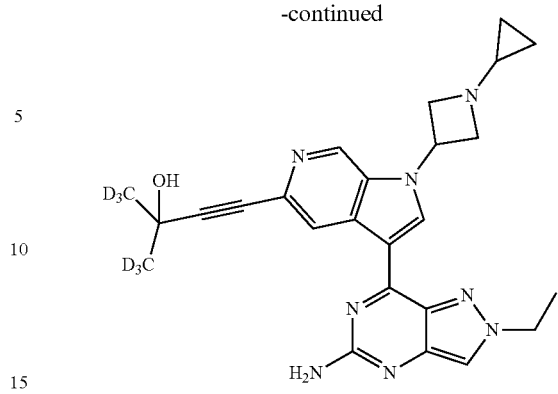

tautomers and stereoisomeric forms thereof, and the pharmaceutically acceptable addition salts, and the solvates thereof.

11. The method according to claims 1 to 6, wherein the compound is in a pharmaceutical composition comprising said compound and a pharmaceutically acceptable carrier or diluent.

12. The method according to claim 10, wherein the compound is in a pharmaceutical composition comprising said compound and a pharmaceutically acceptable carrier or diluent.

* * * * *